(12) United States Patent
Babich

(10) Patent No.: US 12,297,157 B2
(45) Date of Patent: May 13, 2025

(54) ¹⁸F-LABELED PEPTIDE LIGANDS USEFUL IN PET AND CERENKOV LUMINESCENE IMAGING

(71) Applicant: Cornell University, Ithaca, NY (US)

(72) Inventor: John W. Babich, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/772,706

(22) PCT Filed: Dec. 20, 2018

(86) PCT No.: PCT/US2018/066795
§ 371 (c)(1),
(2) Date: Jun. 12, 2020

(87) PCT Pub. No.: WO2019/126497
PCT Pub. Date: Jun. 27, 2019

(65) Prior Publication Data
US 2020/0317588 A1    Oct. 8, 2020

Related U.S. Application Data

(60) Provisional application No. 62/610,132, filed on Dec. 22, 2017.

(51) Int. Cl.
| | | |
|---|---|---|
| C07B 59/00 | (2006.01) | |
| A61K 51/04 | (2006.01) | |
| A61K 51/08 | (2006.01) | |
| C07K 7/08 | (2006.01) | |
| A61K 38/00 | (2006.01) | |

(52) U.S. Cl.
CPC ........ *C07B 59/008* (2013.01); *A61K 51/0497* (2013.01); *A61K 51/083* (2013.01); *C07K 7/086* (2013.01); *A61K 38/00* (2013.01)

(58) Field of Classification Search
CPC .............. C07B 59/008; A61K 51/0497; A61K 51/083; A61K 38/00; C07K 7/086
USPC ...................................................... 424/1.69
See application file for complete search history.

(56) References Cited

U.S. PATENT DOCUMENTS

| | | | |
|---|---|---|---|
| 5,672,662 A | 9/1997 | Harris et al. | |
| 2012/0225089 A1 | 9/2012 | Bouchard et al. | |
| 2013/0343990 A1 | 12/2013 | Luthra et al. | |

FOREIGN PATENT DOCUMENTS

| | | | | |
|---|---|---|---|---|
| CN | 103687627 A | 3/2014 | | |
| EP | 1 099 693 A1 | 5/2001 | | |
| WO | WO-9926551 A1 * | 6/1999 | ........... | A61K 51/121 |
| WO | WO 2012/118909 A1 | 9/2012 | | |
| WO | WO 2018/005625 A1 | 1/2018 | | |

OTHER PUBLICATIONS

Glaser et al. Bioconjugate Chem. 2007, 18, 989-993. (Year: 2007).*
Tatsi et al. EJNMMI Research Feb. 1-13, 2012. (Year: 2012).*
Gonzalez-Muniz et al. J. Med. Chem. 1995, 38, 1015-1021. (Year: 1995).*
Nouel et al. Encrinology 1997, 138, 296-206. (Year: 1997).*
Kelly et al. Eur. J. Nucl. Med. Mol. Imaging 2017, 44, 647-661. (Year: 2017).*
Iddon et al., "Synthesis and in vitro evaluation of [18F]fluoroethyl triazole labelled [Tyr3]octreotate analogues using click chemistry", Bioorganic & Medicinal Chemistry Letters, vol. 21, pp. 3122-3127 (2011).
Leyton et al., "Targeting Somatostatin Receptors: Preclinical Evaluation of Novel 18F-Fluoroethyltriazole-Tyr3-Octreotate Analogs for PET", J Nucl Med, vol. 52, pp. 1441-1448 (2011).
Luthra et al., "Radiolabelled octreotate analogues as PET tracers", US2013/343990 A1, pp. 1-5 (Jan. 2013).
Partial Supplementary European Search Report issued in co-pending European Patent Application No. 18891241.4, dated Oct. 13, 2021.
Chen et al., "[¹⁸F]Fluorethyl Triazole Substituted PSMA Inhibitor Exhibiting Rapid Normal Organ Clearance," *Bioconjug Chem.*, vol. 27, No. 7, pp. 1655-1662 (Jul. 2016).
Pubchem., Somatostatin, Jul. 3, 2007, pp. 1-30 [online], retrieved on Feb. 5, 2019]. Retrieved from the Internet <URL: https://pubchem.ncbi.nlm.nih.gov/compound/16129706#section=TOP> p. 4.
Breeman, et al., "⁶⁸Ga-labeled DOTA-Peptides and ⁶⁸Ga-labeled Radiopharmaceuticals for Positron Emission Tomography: Current Status of Research, Clinical Applications, and Future Perspectives," *Seminars in Nuclear Medicine*, vol. 41, No. 4, pp. 314-321 (Jul. 2011).
International Search Report and Written Opinion issued in International Patent Application No. PCT/US2018/066795, completed Feb. 5, 2019.
Zatelli, et al., "Control of Pituitary Adenoma Cell Proliferation by Somatostatin Analogs, Dopamine Agonists and Novel Chimeric Compounds," *European Journal of Endocrinology*, vol. 156, pp. S29-S35 (2007).
Olberg, et al., "One Step of Radiosynthesis of 6-[(18)F]fluoronicotinic acid 2,3,5,6-tetrafluorophenyl ester ([(18)F]F-Py-TFP): a new prosthetic group for efficient labeling of biomolecules with fluorine-18," *Journal of Medicinal Chemistry*, vol. 53, Issue 4, Feb. 2010, pp. 1732-1740.
Chen, et al., "2-(3-{1-Carboxy-5-[(6-[18F]Fluoro-Pyridine-3-Carbonyl)-Amino]-Pentyl}-Ureido)-Pentanedioic Acid, [18F]DCFPyL, a PSMA-Based PET Imaging Agent for Prostate Cancer," *Clinical Research Cancer*, vol. 17, Issue 24, Dec. 2011, pp. 7645-7653.

(Continued)

*Primary Examiner* — Michael G. Hartley
*Assistant Examiner* — Sean R Donohue
(74) *Attorney, Agent, or Firm* — Foley & Lardner LLP

(57) ABSTRACT

The present technology is directed to compounds, intermediates thereof, compositions thereof, medicaments thereof, and methods related to the imaging of mammalian tissue via ¹⁸F-labeled peptide ligands disclosed herein.

3 Claims, No Drawings

(56) References Cited

OTHER PUBLICATIONS

Robertson, et al., "Optical imaging of Cerenkov light generation from positron-emitting radiotracers," Phys Med Biol, vol. 54, Issue 16, 2009, pp. 355-365.

Grootendorst, et al., "Cerenkov luminescence imaging (CLI) for image-guided cancer surgery," Clin Transl Imagine, vol. 4, Mar. 24, 2016, pp. 353-366.

Office Action issued in co-pending Chinese Patent Application No. 201880082163.5, dated May 9, 2022.

Chen et al., "Novel molecular "add-on" based on Evans Blue confers superior pharmacokinetics and transforms drugs to theranostic agents", Journal of Nuclear Medicine, vol. 61, 2020, 44 pages.

Guillaume, et al., "Scavenging Strategy for Specific Activity Improvement: application to a new CXCR4-Specific Cyclopentapeptide Positron Emission Tomography Tracer: Scavenging for higher specific activity applied to an FC131 Analogue", Journal of Labelled Compounds and Radiopharmaceuticals, vol. 56, No. 13, pp. 679-685 (Nov. 2013).

Examination Report issued in Australia Patent Application No. 2018389100, dated Mar. 27, 2024.

\* cited by examiner

[18]F-LABELED PEPTIDE LIGANDS USEFUL IN PET AND CERENKOV LUMINESCENE IMAGING

CROSS-REFERENCE TO RELATED APPLICATIONS

This application is a U.S. National Phase Application under 35 U.S.C. § 371 of International Application No. PCT/US2018/066795, filed on Dec. 20, 2018, which claims the benefit of the priority date of U.S. Provisional Application No. 62/610,132, filed Dec. 22, 2017, the entirety of the disclosures of each of which are hereby incorporated by reference for any and all purposes.

FIELD

The present technology is directed to compounds, compositions, and methods related to the imaging of mammalian tissues via $^{18}$F-labeled peptide ligands, such as a $^{18}$F-labeled somatostatin receptor agonist, a $^{18}$F-labeled bombesin receptor agonist, and a $^{18}$F-labeled seprase binding compound, as more fully disclosed herein.

SUMMARY

The present technology provides $^{18}$F-labeled peptide ligands useful in imaging e.g., of mammalian tissues, such as via positron emission tomography (PET) and/or Cerenkov luminescene imaging. Furthermore, the present technology provides advanced intermediates that allow for facile and rapid production of the $^{18}$F-labeled peptide ligands of the present technology, allowing for relatively easy production of the compounds of the present technology prior to use.

Thus, in an aspect, the present technology provides $^{18}$F-labeled somatostatin receptor agonists useful in, e.g., positron emission tomography (PET) and/or Cerenkov luminescene imaging of somatostatin receptor positive tumors. Such $^{18}$F-labeled somatostatin receptor agonists include a somatostatin receptor agonist with a primary amine, secondary amine, $NH_2$ of a guanadinyl group, or $NH_2$ of an amidinyl group of the somatostatin receptor agonist covalently bonded to $W^1$ or a carboxylic acid or amide of the somatostatin receptor agonist is modified to a $—C(O)Y^1$ group, where $W^1$ is

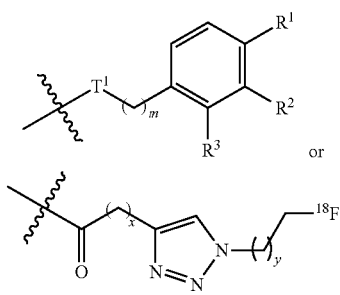

and $Y^1$ is

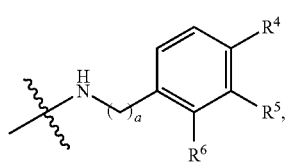

wherein $T^1$ is $—C(O)—$ or $—C(O)NH—$, one of $R^1$, $R^2$, and $R^3$ and one of $R^4$, $R^5$, and $R^6$ is

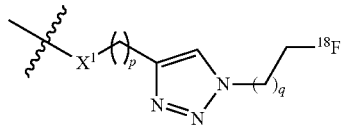

and the remaining two of $R^1$, $R^2$, and $R^3$ are each H and the remaining two of $R^4$, $R^5$, and $R^6$ are each H; $X^1$ is absent, O, S, or NH; m and a are each independently 0, 1, 2, or 3; n is 1 or 2; p is 0, 1, 2, or 3, provided that when p is 0 then $X^1$ is absent; q is 1 or 2; x is 0, 1, 2, or 3; and y is 1 or 2, or a pharmaceutically acceptable salt and/or a solvate thereof.

In an aspect, the present technology provides $^{18}$F-labeled bombesin receptor agonists (such as BBR-1 agonists, BBR-2 agonists, and BBR-3 agonists) useful in, e.g., positron emission tomography (PET) and/or Cerenkov luminescene imaging of bombesin receptor positive tissues. Such $^{18}$F-labeled bombesin receptor agonists include a bombesin receptor agonist with a primary amine, secondary amine, $NH_2$ of a guanadinyl group, or $NH_2$ of an amidinyl group of the bombesin receptor agonist covalently bonded to W' or a carboxylic acid or amide of the bombesin receptor agonist that is modified to a $—C(O)Y'$ group, where W' is

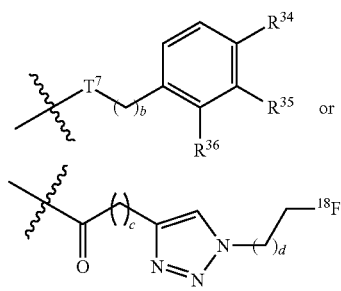

and Y' is

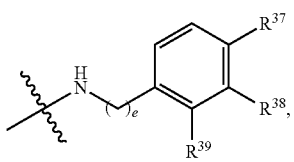

wherein $T^7$ is $—C(O)—$ or $—C(O)NH—$, one of $R^{34}$, $R^{35}$, and $R^{36}$ and one of $R^{37}$, $R^{38}$, and $R^{39}$ is

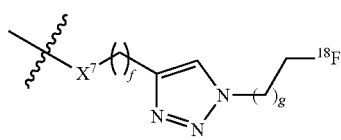

and the remaining two of $R^{34}$, $R^{35}$, and $R^{36}$ are each H and the remaining two of $R^{37}$, $R^{38}$, and $R^{39}$ are each H; $X^6$ is absent, O, S, or NH; b and e are each independently 0, 1, 2, or 3; f is 0, 1, 2, or 3, provided that when f is 0 then $X^7$ is absent; g is 1 or 2; c is 0, 1, 2, or 3; and d is 1 or 2.

In an aspect, the present technology provides $^{18}$F-labeled peptides that bind to seprase ("seprase binding compounds") useful in, e.g., positron emission tomography (PET) and/or Cerenkov luminescene imaging of seprase-bearing tissues. Such seprase binding compounds include seprase inhibitors. A $^{18}$F-labeled seprase binding compound includes a seprase binding compound with a primary amine, secondary amine, $NH_2$ of a guanadinyl group, or $NH_2$ of an amidinyl group covalently bonded to $W^{15}$ or a carboxylic acid or amide of the seprase binding compound that is modified to a —C(O)$Y^{11}$ group, where $W^{15}$ is

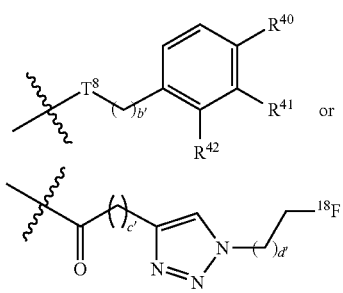

and $Y^{11}$ is

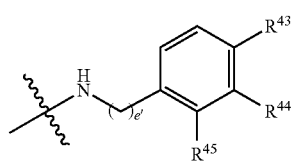

wherein $T^8$ is —C(O)— or —C(O)NH—, one of $R^{34}$, $R^{35}$, and $R^{36}$ and one of $R^{37}$, $R^{38}$, and $R^{39}$ is

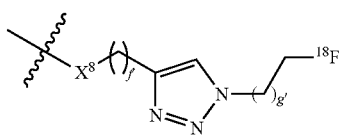

and the remaining two of $R^{40}$, $R^{41}$, and $R^{42}$ are each H and the remaining two of $R^{43}$, $R^{44}$, and $R^{45}$ are each H; $X^8$ is absent, O, S, or NH; b' and e' are each independently 0, 1, 2, or 3; f is 0, 1, 2, or 3, provided that when f is 0 then $X^8$ is absent; g' is 1 or 2; c' is 0, 1, 2, or 3; and d' is 1 or 2.

Intermediates for preparing any one of $^{18}$F-labeled peptide ligands of the present technology are also provided. Because $^{18}$F compounds are typically generated in a relatively short time period prior to use, the intermediates of the present technology provide a substantial improvement to available resources and greatly facilitate rapid production of the targeted imaging compounds of the present technology with high radiochemical yield.

In a related aspect, a composition is provided that includes any one of $^{18}$F-labeled peptide ligands of the present technology and a pharmaceutically acceptable carrier.

DETAILED DESCRIPTION

In various aspects, the present technology provides compounds and methods for imaging mammalian tissues. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "amino acid" includes naturally-occurring α-amino acids and synthetic α-amino acids (e.g., 2-amino-2-phenylacetic acid, also referred to as phenylglycine), as well as α-amino acid analogues and amino acid mimetics that function in a manner similar to the naturally-occurring amino acids. The term further includes both L and D forms of such α-amino acids unless a specific stereoisomer is indicated. Naturally-occurring amino acids are those encoded by the genetic code, as well as those amino acids that are later modified, e.g., hydroxyproline, γ-carboxyglutamate, and O-phosphoserine. Amino acid analogues refer to compounds that have the same basic chemical structure as a naturally-occurring amino acid, e.g., an α-carbon bearing an organic group, e.g., homoserine, norleucine, methionine sulfoxide, methionine methyl sulfonium. Such analogues may have modified organic groups (e.g., norleucine) or modified peptide backbones, but retain the same basic chemical structure as a naturally-occurring amino acid. Amino acid mimetics refer to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art, as well as synthetic amino acids.

Generally, reference to a certain element such as hydrogen or H is meant to include all isotopes of that element. For example, if an R group is defined to include hydrogen or H, it also includes deuterium and tritium. Compounds comprising radioisotopes such as tritium, $^{14}$C, $^{32}$P, and $^{35}$S are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., SF$_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds.

Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups may be substituted or unsubstituted. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl(pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$. A "hydroxyalkyl" group is a hydroxyl-substituted alkyl group, such as HO—CH$_2$—.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, trifluoroacetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

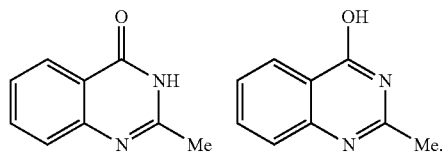

As another example, guanidines may exhibit the following isomeric forms in protic organic solution, also referred to as tautomers of each other:

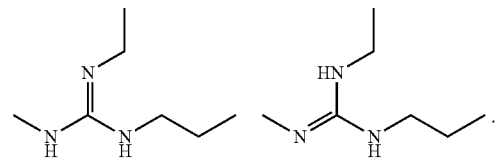

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

The Present Technology

Somatostatin, illustrated in Scheme 1, is a peptide hormone that regulates the endocrine system and affects neurotransmission and cell proliferation via interaction with G protein-coupled somatostatin receptors and inhibition of the release of numerous secondary hormones. Somatostatin has two active forms produced by alternative cleavage of a single preproprotein. There are five known somatostatin receptors, all being G protein-coupled seven transmembrane receptors: SST1 (SSTR1); SST2 (SSTR2); SST3 (SSTR3); SST4 (SSTR4); and SST5 (SSTR5). Exemplary somatostatin receptor agonists include somatostatin itself, lanreotide, octreotate, octreotide, pasireotide, and vapreotide.

Scheme 1.

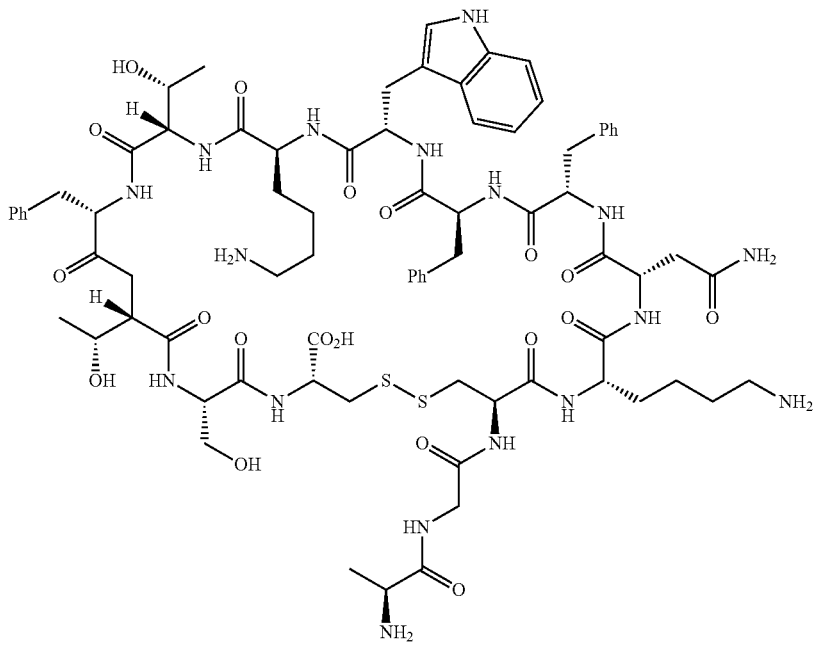

Many neuroendocrine tumors express SSTR2 and the other somatostatin receptors. Long acting somatostatin agonists (e.g., Octreotide, Lanreotide) are used to stimulate the SSTR2 receptors, and thus to inhibit further tumor proliferation. See, Zatelli M C, et al., (April 2007). "Control of pituitary adenoma cell proliferation by somatostatin analogs, dopamine agonists and novel chimeric compounds". European Journal of Endocrinology/European Federation of Endocrine Societies. 156 Suppl 1: S29-35. Octreotide is an octapeptide that mimics natural somatostatin but has a significantly longer half-life in vivo. Octreotide is used for the treatment of growth hormone producing tumors (acromegaly and gigantism), when surgery is contraindicated, pituitary tumors that secrete thyroid stimulating hormone (thyrotropinoma), diarrhea and flushing episodes associated with carcinoid syndrome, and diarrhea in people with vasoactive intestinal peptide-secreting tumors (VIPomas). Lanreotide is used in the management of acromegaly and symptoms caused by neuroendocrine tumors, most notably carcinoid syndrome. Pasireotide is a somatostatin analog with an increased affinity to SSTR5 compared to other somatostatin agonists and is approved for treatment of Cushing's disease and acromegaly. Vapreotide is used in the treatment of esophageal variceal bleeding in patients with cirrhotic liver disease and AIDS-related diarrhea.

Bombesin is a peptide originally isolated from the skin of the European fire-bellied toad (Bombina bombina). In addition to stimulating gastrin release from G cells, bombesin activates at least three different G-protein-coupled receptors: BBR1, BBR2, and BBR3, where such activity includes agonism of such receptors in the brain. Bombesin is also a tumor marker for small cell carcinoma of lung, gastric cancer, pancreatic cancer, and neuroblastoma.

Seprase (or Fibroblast Activation Protein (FAP)) is an integral membrane serine peptidase. In addition to gelatinase activity, seprase has a dual function in tumour progression. Seprase promotes cell invasiveness towards the ECM and also supports tumour growth and proliferation.

Small molecule ligands have been described as single photon emission computed tomography (SPECT) or positron emission tomography (PET) imaging agents for cancers such as prostate cancer, and several of them are undergoing clinical investigation in man. For example, for, seven prostate-specific membrane antigen (PSMA) ligands have entered or are in Phase I/II/III clinical trials in the United States and/or Europe: (i) radioiodinated MIP-1095 (1-123 for SPECT/CT and 1-124 for PET/CT) and MIP-1072 (1-123 for SPECT/CT), developed by Molecular Insight Pharmaceuticals, Inc., (ii) $^{99m}$Tc-MIP-1404 and $^{99m}$Tc-MIP-1405, two further SPECT imaging agents emerging from the Molecular Insight Pharmaceuticals platform, (iii) [$^{68}$Ga]Ga-PSMA-HBED-CC (also known as [$^{68}$Ga]PSMA-11 and [$^{68}$Ga]DKFZ-PSMA-11) for PET/CT, and (iv) [$^{18}$F]DCFBC and its next generation derivative [$^{18}$F]DCFPyL for PET/CT. Newly introduced compounds to undergo first-in-man evaluation include $^{68}$Ga-DKFZ-617, developed to be a theranostic ligand and evaluated in a therapeutic context as $^{177}$Lu-DKFZ-617, and the structurally related $^{68}$Ga-CHX-A"-DTPA.

The greater sensitivity and higher spatial resolution of PET relative to SPECT has made this technique the preferred imaging platform in a number of clinical environments. Fluorine-18 and gallium-68 are preferred to iodine-124 because of their shorter half lives, associated lower radiation dose and higher efficiency of positron emission (97% and 89% vs. 23%, respectively). Furthermore, iodine-124 scans require complex reconstruction algorithms to minimize the signal-to-noise ratio, which, in combination with the long half-life of iodine-124 ($t_{1/2}$=4.18 d) and the undesired emission of beta particles, is often a poor match for the pharmacokinetics of small molecules. In addition, gallium-68 is currently produced from a $^{68}$Ge/$^{68}$Ga generator, enabling its use in single batch syntheses in radiopharmacies independent of access to a cyclotron, and chelation of gallium-68 is both clean and rapid under conditions that are compatible with most small molecule and peptides. For example, these considerations have contributed to the emergence of [$^{68}$Ga]Ga-PSMA-HBED-CC as the most widely used PSMA PET radiotracer currently in clinical development.

Cerenkov luminescence imaging (CLI) is an imaging modality for image-guided surgery in general, and especially in regard to surgical margins in particular. CLI is based on the detection of Cerenkov photons emitted by PET imaging agents. Cerenkov photons are emitted by a charged particle (positron or electron) when travelling through a dielectric medium at a velocity greater than the velocity of light in that medium. The Cerenkov phenomenon seems to have been first observed by Marie Curie in the late 19th century. In her biography, she describes observing a pale blue glow from the radium-containing bottles in her laboratory. The first person to systematically describe Cerenkov radiation was Pavel Cerenkov, and together with Il'ja Mikhailovic Frank and Igor Yevgenyevich Tamm who developed the theoretical framework, they won the Nobel Prize in Physics in 1958 for their contribution to the discovery of the Cerenkov effect. In the lay mind, Cerenkov radiation is known as the blue glow in the cooling water basins that surround nuclear reactors. By detecting the optical photons from PET imaging tracers, CLI combines optical and molecular imaging. CLI with PET agents has been used to image cancer in vivo, and since then, this technology has rapidly emerged in the field of biomedical imaging. See, e.g., Robertson R, Germanos M S, Li C, Mitchell G S, Cherry S R, Silva M D. Optical imaging of Cerenkov light generation from positron-emitting radiotracers. Phys Med Biol 2009, 54(16):N355-365 (doi:10.1088/0031-9155/54/16/n01) and M. R. Grootendorst M R, Cariati M, Kothari A, Tuch D S, •Purushotham A. Cerenkov luminescence imaging (CLI) for image-guided cancer surgery. Clin Transl Imaging 2016, 4:353-366 (doi: 10.1007/s40336-016-0183-x). CLI images may be acquired by detecting the Cerenkov light from positron emitting radiotracers using ultra-high-sensitivity optical cameras such as electron-multiplying charge-coupled device (EMCCD) cameras. The CLI image can be analyzed semiquantitatively in photon radiance. Several studies have shown a strong correlation between CLI and PET for different radiopharmaceuticals in vitro, ex vivo, and in vivo.

The present technology addresses the need to image diseases via use of peptides with affinity e.g., to diseased tissue, via $^{18}$F-labeled peptide ligands. Furthermore, the present technology provides advanced intermediates that allow for facile and rapid production of the $^{18}$F-labeled peptide ligands of the present technology, allowing for relatively easy production of the compounds of the present technology prior to use.

Thus, in an aspect, the present technology provides $^{18}$F-labeled somatostatin receptor agonists (herein also referred to as "compounds of the present technology") useful in, e.g., positron emission tomography (PET) and/or Cerenkov luminescene imaging of somatostatin receptor positive tumors. Such $^{18}$F-labeled somatostatin receptor agonists include a somatostatin receptor agonist with a primary amine, secondary amine, $NH_2$ of a guanadinyl group, or $NH_2$ of an amidinyl group of the somatostatin receptor agonist covalently bonded to $W^1$ or a carboxylic acid or amide of the somatostatin receptor agonist is modified to a $—C(O)Y^1$ group, where $W^1$ is

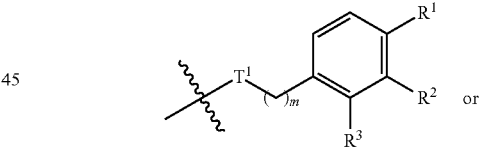

or

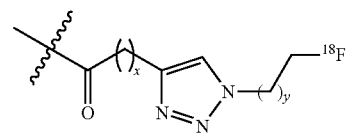

and $Y^1$ is

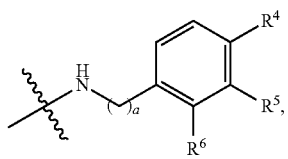

wherein $T^1$ is —C(O)— or —C(O)NH—, one of $R^1$, $R^2$, and $R^3$ and one of $R^4$, $R^5$, and $R^6$ is

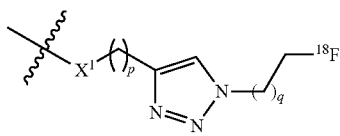

and the remaining two of $R^1$, $R^2$, and $R^3$ are each H and the remaining two of $R^4$, $R^5$, and $R^6$ are each H; $X^1$ is absent, O, S, or NH; m and a are each independently 0, 1, 2, or 3; n is 1 or 2; p is 0, 1, 2, or 3, provided that when p is 0 then $X^1$ is absent; q is 1 or 2; x is 0, 1, 2, or 3; and y is 1 or 2, or a pharmaceutically acceptable salt and/or a solvate thereof.

Exemplary $^{18}$F-labeled somatostatin receptor agonists include, but are not limited to, compounds of Formulas I-V as illustrated below. Thus, in any embodiment herein, the $^{18}$F-labeled somatostatin receptor agonist may be a compound of Formula I

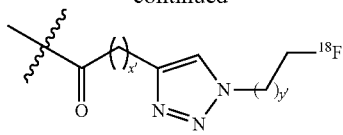

or one of $Y^2$ and $Y^3$ is

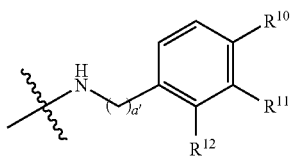

and the remaining $W^2$, $W^3$, $W^4$ are each independently H and the remaining $Y^2$ and $Y^3$ is OH or $NH_2$, wherein $T^2$ is —C(O)— or —C(O)NH—, one of $R^7$, $R^8$, and $R^9$ and one of $R^{10}$, $R^{11}$, and $R^{12}$ is (I)

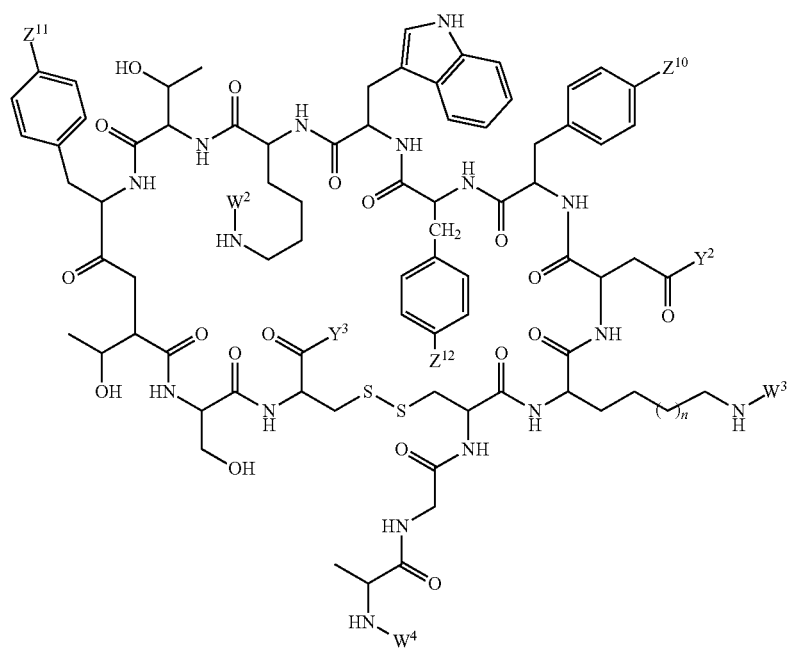

or a pharmaceutically acceptable salt and/or solvate thereof, wherein $Z^{10}$ and $Z^{11}$ are each independently H or OH;
one of $W^2$, $W^3$, and $W^4$ is

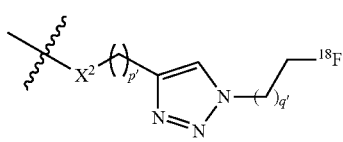

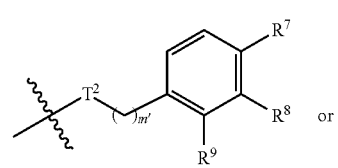

and the remaining two of $R^7$, $R^8$, and $R^9$ are each H and the remaining two of $R^{10}$, $R^{11}$, and $R^{12}$ are each H; $X^2$ is absent, O, S, or NH; m' and a' are each independently 0, 1, 2, or 3; n is 0 or 1; p' is 0, 1, 2, or 3, provided that when p' is 0 then $X^2$ is absent; q' is 1 or 2; x' is 0, 1, 2, or 3; and y' is 1 or 2.

In any embodiment herein, the $^{18}$F-labeled somatostatin receptor agonist of Formula I may be of Formula IA

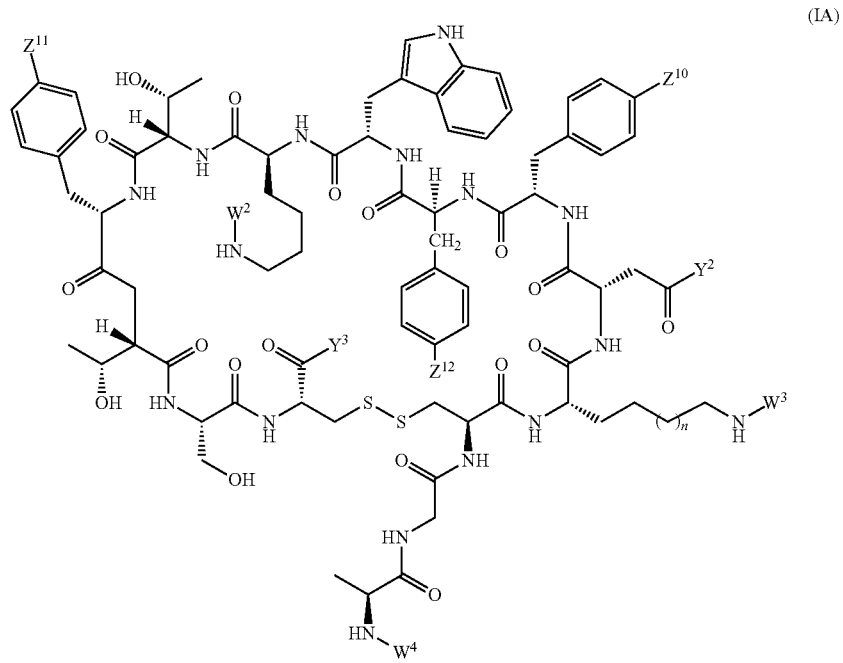
(IA)
or a pharmaceutically acceptable salt and/or solvate thereof.
In any embodiment herein, the $^{18}$F-labeled somatostatin receptor agonist of Formula I may be of Formula IB
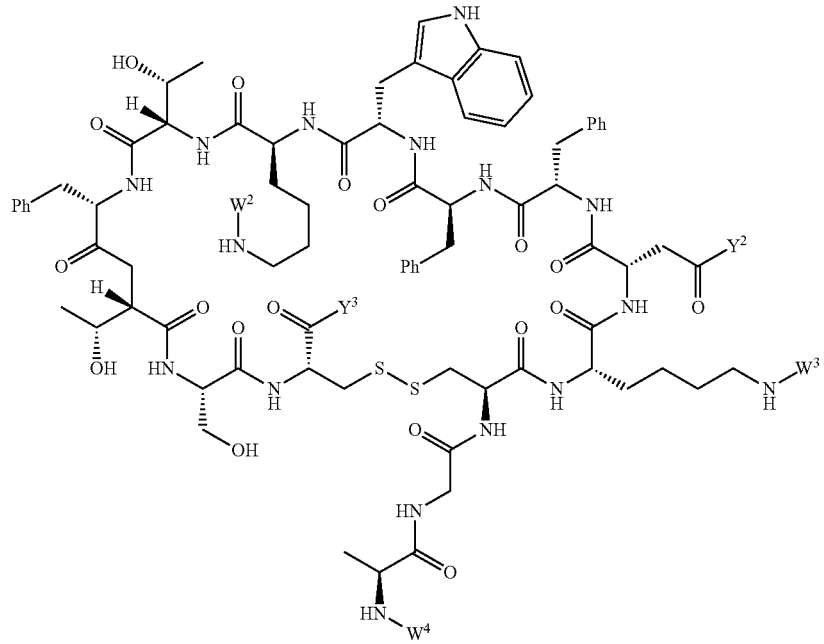
(IB)
or a pharmaceutically acceptable salt and/or solvate thereof.

In any embodiment herein, the $^{18}$F-labeled somatostatin receptor agonist may be a compound of Formula II

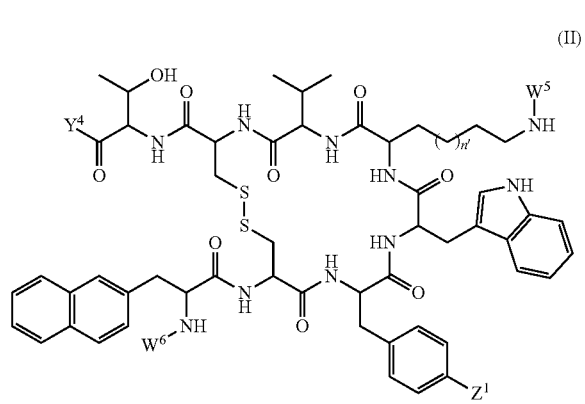

(II)

or a pharmaceutically acceptable salt and/or solvate thereof, wherein
one of $W^5$ and $W^6$ is

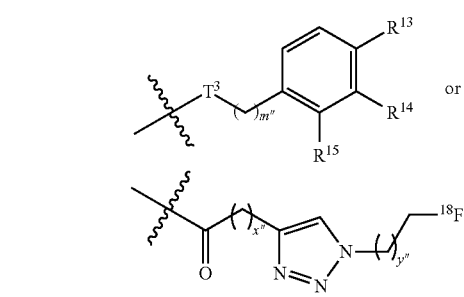

or $Y^4$ is

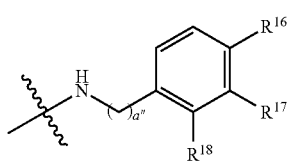

and the remaining $W^5$ and $W^6$ are each independently H and the remaining $Y^4$ (i.e., if not the structure indicated above) is OH or $NH_2$, wherein $T^3$ is —C(O)— or —C(O)NH—, one of $R^{13}$, $R^{14}$, and $R^{15}$ and one of $R^{16}$, $R^{17}$, and $R^{18}$ is

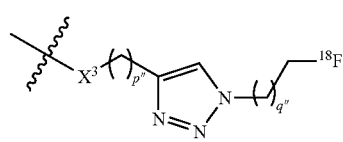

and the remaining two of $R^{13}$, $R^{14}$, and $R^{15}$ are each H and the remaining two of $R^{16}$, $R^{17}$, and $R^{18}$ are each H; $X^3$ is absent, O, S, or NH; m'' and a'' are each independently 0, 1, 2, or 3; n' is 0 or 1; p'' is 0, 1, 2, or 3, provided that when p'' is 0 then $X^3$ is absent; q'' is 1 or 2; x'' is 0, 1, 2, or 3; and y'' is 1 or 2; and $Z^1$ is H or OH. In any embodiment herein, the $^{18}$F-labeled somatostatin receptor agonist of Formula II may be a compound of Formula IIA

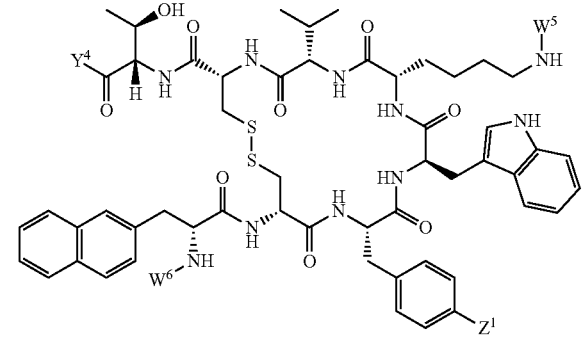

(IIA)

or a pharmaceutically acceptable salt and/or solvate thereof.

In any embodiment herein, the $^{18}$F-labeled somatostatin receptor agonist may be a compound of Formula III

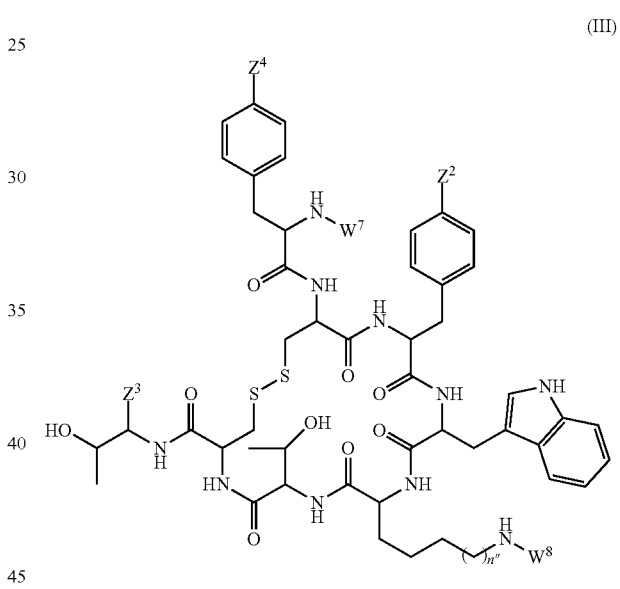

(III)

or a pharmaceutically acceptable salt and/or solvate thereof, wherein
$Z^2$ and $Z^4$ are each independently H or OH;
$Z^3$ is $C(O)Y^5$ or $CH_2OH$;
one of $W^7$ and $W^8$ is

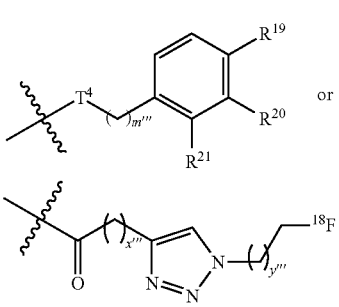

or $Y^5$ is

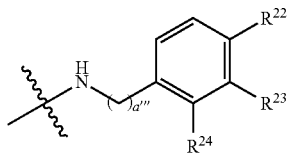

and the remaining $W^7$ and $W^8$ are each independently H and the remaining $Y^5$ (i.e., if not the structure indicated above) is OH or $NH_2$, wherein $T^4$ is —C(O)— or —C(O)NH—, one of $R^{19}$, $R^{20}$, and $R^{21}$ and one of $R^{22}$, $R^{23}$, and $R^{24}$ is

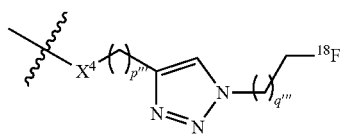

and the remaining two of $R^{19}$, $R^{20}$, and $R^{21}$ are each H and the remaining two of $R^{22}$, $R^{23}$, and $R^{24}$ are each H; $X^4$ is absent, O, S, or NH; m''' and a''' are each independently 0, 1, 2, or 3; n'' is 0 or 1; p''' is 0, 1, 2, or 3, provided that when p''' is 0 then $X^3$ is absent; q''' is 1 or 2; x''' is 0, 1, 2, or 3; and y''' is 1 or 2.

In any embodiment herein, the $^{18}F$-labeled somatostatin receptor agonist of Formula III may be a compound of Formula IIIA

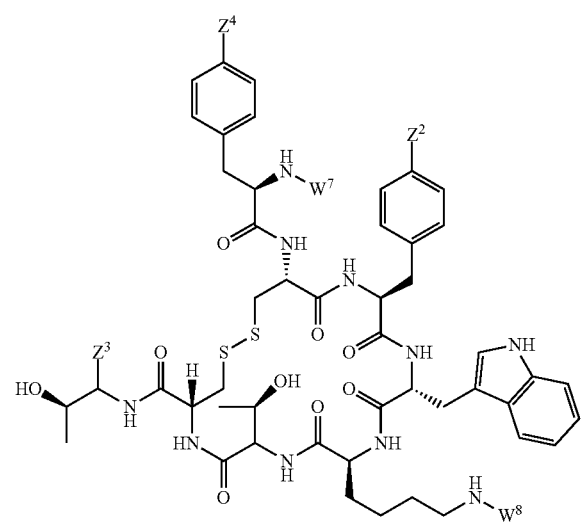

(IIIA)

or a pharmaceutically acceptable salt and/or solvate thereof.

In any embodiment herein, the $^{18}F$-labeled somatostatin receptor agonist may be a compound of Formula IV

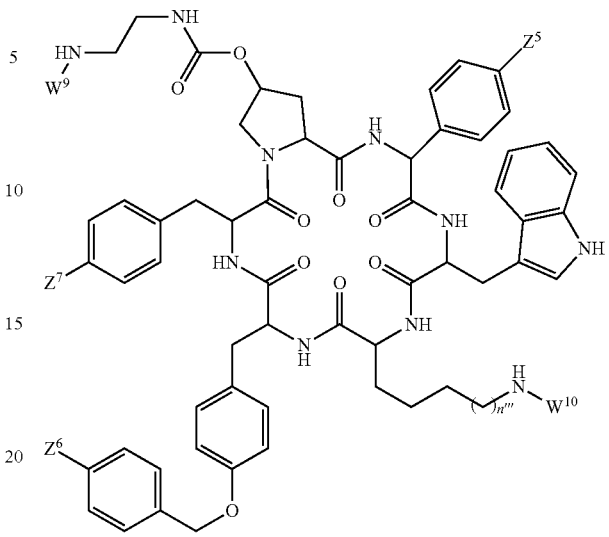

(IV)

or a pharmaceutically acceptable salt and/or solvate thereof, wherein one of $W^9$ and $W^{10}$ is

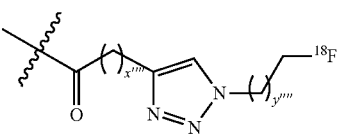 or

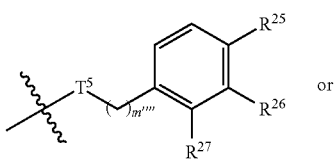

remaining one of $W^9$ and $W^{10}$ is H, wherein $T^5$ is —(O)— or —C(O)NH—, one of $R^{25}$, $R^{26}$, and $R^{27}$ is

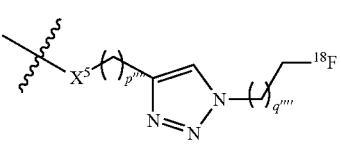

and the remaining two of $R^{25}$, $R^{26}$, and $R^{27}$ are each H; $X^5$ is absent, O, S, or NH; m'''' is 0, 1, 2, or 3; n''' is 0 or 1; p'''' is 0, 1, 2, or 3, provided that when p'''' is 0 then $X^5$ is absent; q'''' is 1 or 2; x'''' is 0, 1, 2, or 3; y'''' is 1 or 2; and $Z^5$, $Z^6$, and $Z^7$ are each independently H or OH. In any embodiment herein, the compound of Formula IV may be a compound of Formula IVA (IVA)

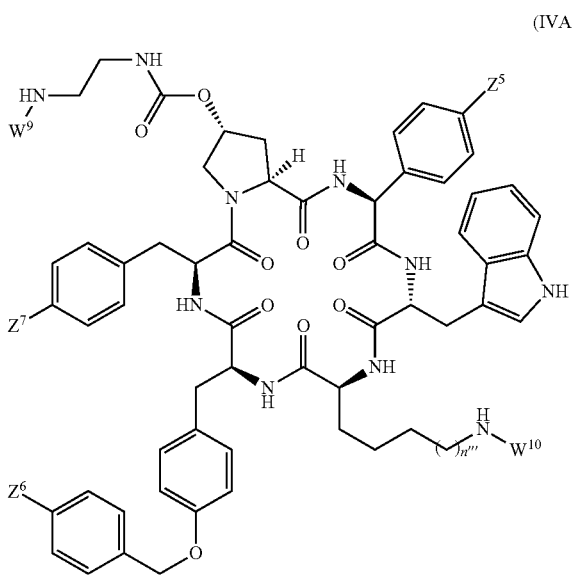

or a pharmaceutically acceptable salt and/or a solvate thereof.

In any embodiment herein, the $^{18}$F-labeled somatostatin receptor agonist may be a compound of Formula V (V)

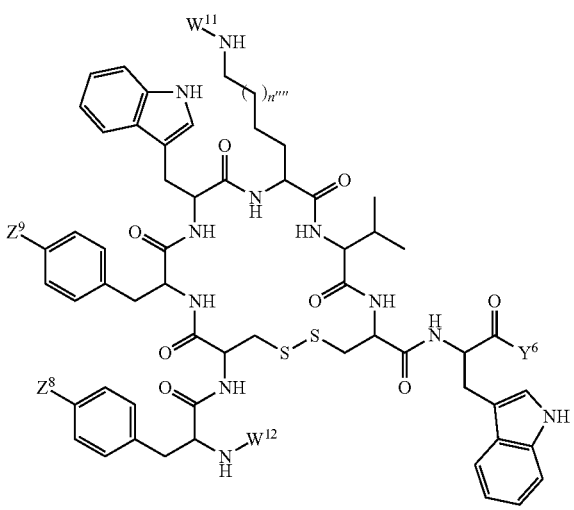

or a pharmaceutically acceptable salt and/or solvate thereof, wherein
one of $W^{11}$ and $W^{12}$ is

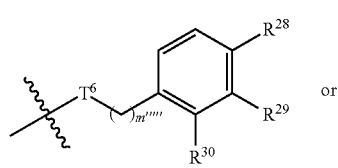 or

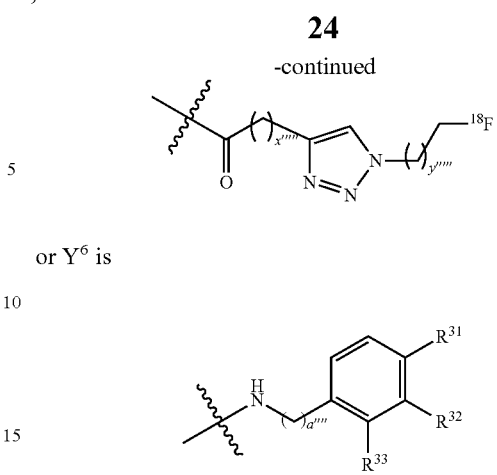

or $Y^6$ is and the remaining $W^{11}$ and $W^{12}$ are each independently H and the remaining $Y^6$ (i.e., if not the structure indicated above) is OH or $NH_2$, wherein $T^6$ is —C(O)— or —C(O)NH—, one of $R^{28}$, $R^{29}$, and $R^{30}$ and one of $R^{31}$, $R^{32}$, and $R^{33}$ is

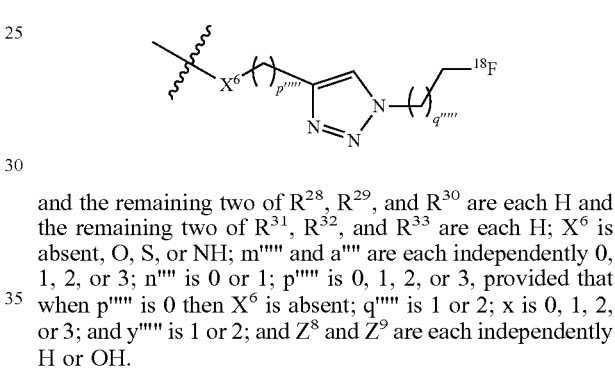

and the remaining two of $R^{28}$, $R^{29}$, and $R^{30}$ are each H and the remaining two of $R^{31}$, $R^{32}$, and $R^{33}$ are each H; $X^6$ is absent, O, S, or NH; m'''' and a'''' are each independently 0, 1, 2, or 3; n'''' is 0 or 1; p'''' is 0, 1, 2, or 3, provided that when p'''' is 0 then $X^6$ is absent; q'''' is 1 or 2; x is 0, 1, 2, or 3; and y'''' is 1 or 2; and $Z^8$ and $Z^9$ are each independently H or OH.

In any embodiment herein, the compound of Formula V may be a compound of Formula VA (VA)

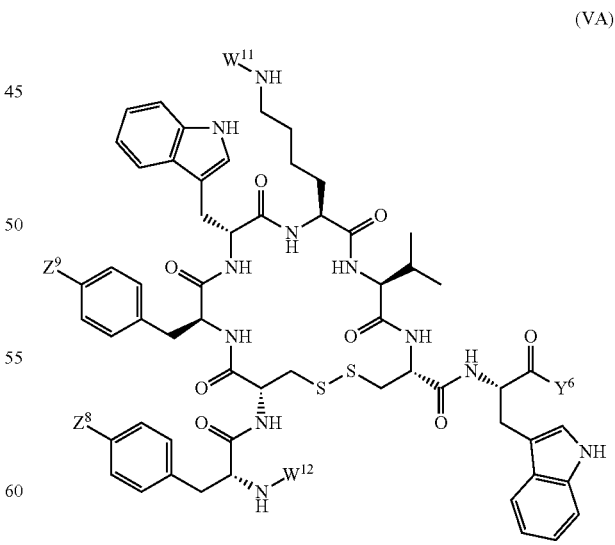

or a pharmaceutically acceptable salt and/or a solvate thereof.

In an aspect, the present technology provides $^{18}$F-labeled bombesin receptor agonists (such as BBR-1 agonists, BBR-2 agonists, and BBR-3 agonists) useful in, e.g., positron emission tomography (PET) and/or Cerenkov luminescene imaging of bombesin receptor positive tissues. Such ¹⁸F-labeled bombesin receptor agonists include a bombesin receptor agonist with a primary amine, secondary amine, $NH_2$ of a guanadinyl group, or $NH_2$ of an amidinyl group of the bombesin receptor agonist covalently bonded to W' or a carboxylic acid or amide of the bombesin receptor agonist that is modified to a —C(O)Y' group, where W' is

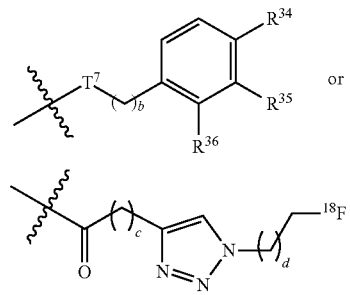

or

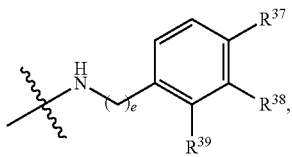

wherein $T^7$ is —C(O)— or —C(O)NH—, one of $R^{34}$, $R^{35}$, and $R^{36}$ and one of $R^{37}$, $R^{38}$, and $R^{39}$ is and the remaining two of $R^{34}$, $R^{35}$, and $R^{36}$ are each H and the remaining two of $R^{37}$, $R^{38}$, and $R^{39}$ are each H; $X^6$ is absent, O, S, or NH; b and e are each independently 0, 1, 2, or 3; f is 0, 1, 2, or 3, provided that when f is 0 then $X^7$ is absent; g is 1 or 2; c is 0, 1, 2, or 3; and d is 1 or 2.

Exemplary ¹⁸F-labeled bombesin receptor agonists include, but are not limited to, compounds of Formula VI and Formula VIA (VI)

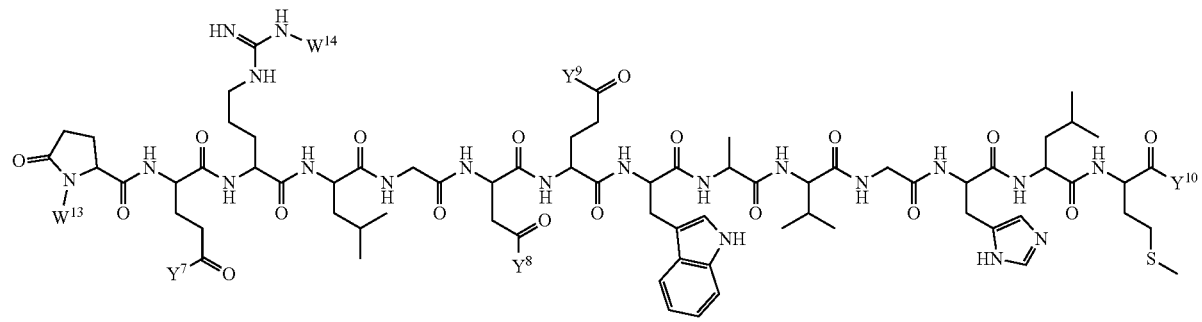

(VIA)

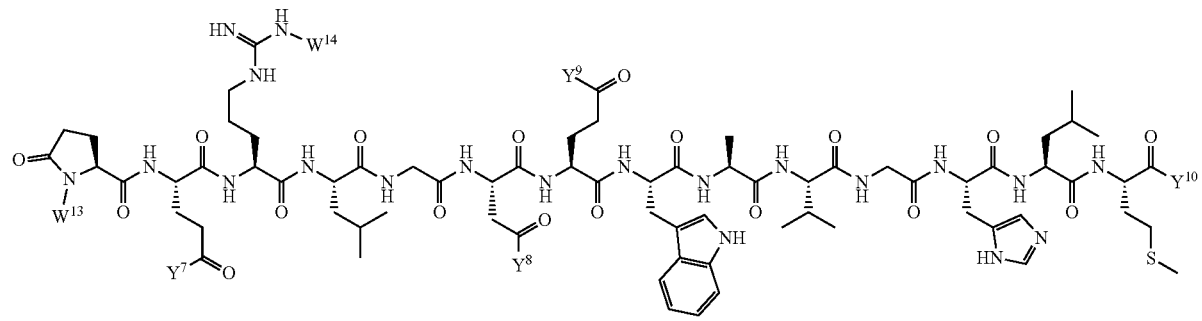

or a pharmaceutically acceptable salt and/or solvate thereof, where independently in each of Formulas VI and VIA, one of $W^{13}$ and $W^{14}$ is

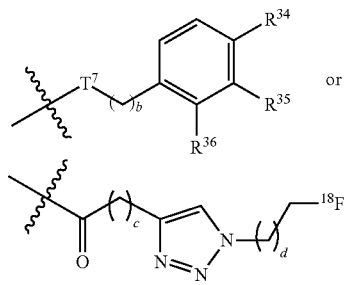

or one of $Y^7$, $Y^8$, $Y^9$, and $Y^{10}$ is

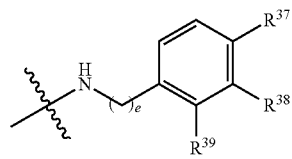

and the remaining $W^{13}$ and $W^{14}$ are each independently H and the remaining $Y^7$, $Y^8$, $Y^9$, and $Y^{10}$ (i.e., if not the structure indicated above) is OH or $NH_2$, wherein $T^7$ is —C(O)— or —C(O)NH—, one of $R^{28}$, $R^{29}$, and $R^{30}$ and one of $R^{31}$, $R^{32}$, and $R^{33}$ is

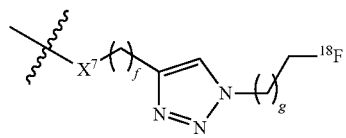

and the remaining two of $R^{28}$, $R^{29}$, and $R^{30}$ are each H and the remaining two of $R^{31}$, $R^{32}$, and $R^{33}$ are each H; $X^6$ is absent, O, S, or NH; b and e are each independently 0, 1, 2, or 3; f is 0, 1, 2, or 3, provided that when f is 0 then $X^7$ is absent; g is 1 or 2; c is 0, 1, 2, or 3; and d is 1 or 2.

In an aspect, the present technology provides $^{18}F$-labeled peptides that bind to seprase ("seprase binding compounds") useful in, e.g., positron emission tomography (PET) and/or Cerenkov luminescene imaging of seprase-bearing tissues. Such seprase binding compounds include seprase inhibitors. A $^{18}F$-labeled seprase binding compound includes a seprase binding compound with a primary amine, secondary amine, $NH_2$ of a guanadinyl group, or $NH_2$ of an amidinyl group covalently bonded to $W^{15}$ or a carboxylic acid or amide of the seprase binding compound that is modified to a —C(O)$Y^{11}$ group, where $W^{15}$ is

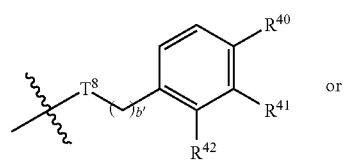

-continued

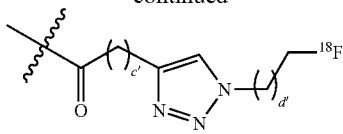

and $Y^{11}$ is

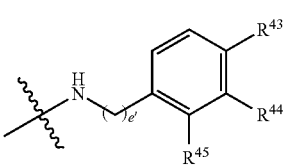

wherein $T^8$ is —C(O)— or —C(O)NH—, one of $R^{34}$, $R^{35}$, and $R^{36}$ and one of $R^{37}$, $R^{38}$, and $R^{39}$ is

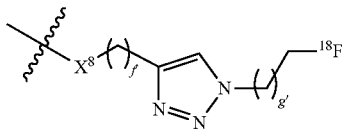

and the remaining two of $R^{40}$, $R^{41}$, and $R^{42}$ are each H and the remaining two of $R^{43}$, $R^{44}$, and $R^{45}$ are each H; $X^8$ is absent, O, S, or NH; b' and e' are each independently 0, 1, 2, or 3; f' is 0, 1, 2, or 3, provided that when f' is 0 then $X^8$ is absent; g' is 1 or 2; c' is 0, 1, 2, or 3; and d' is 1 or 2.

Intermediates for preparing any one of $^{18}F$-labeled peptide ligands of the present technology are also provided. Because $^{18}F$ compounds are typically generated in a relatively short time period prior to use, the intermediates of the present technology provide a substantial improvement to available resources and greatly facilitate rapid production of the targeted imaging compounds of the present technology with high radiochemical yield.

Particularly useful intermediates for producing a $^{18}F$-labeled somatostatin receptor agonist of the present technology include, but is not limited to, an intermediate that includes a somatostatin receptor agonist with a primary amine, secondary amine, $NH_2$ of a guanadinyl group, or $NH_2$ of an amidinyl group covalently bonded to $W^{16}$ (described infra) or a carboxylic acid or amide of the somatostatin receptor agonist is modified to a —C(O)$Y^{12}$ group ($Y^{12}$ is described infra). Exemplary intermediates include (i) an intermediate of Formula VII, an intermediate of Formula VIIA, and an intermediate of Formula VIIB that respectively correspond to the compound of Formula I, Formula IA, and Formula IB with the exception of the recited groups of $W^2$, $W^3$, $W^4$, $Y^2$, and $Y^3$, where in Formulas VII, VIIA, and VIIB one of $W^2$, $W^3$, and $W^4$ is $W^{16}$ or one of $Y^2$ and $Y^3$ is $Y^{12}$ and the remaining $W^2$, $W^3$, and $W^4$ (i.e., when not $W^{16}$) are each independently H and the remaining $Y^2$ and $Y^3$ (i.e., when not $Y^{12}$) are each independently OH or $NH_2$;

(ii) an intermediate of Formula VIII and an intermediate of Formula VIIIA that respectively correspond to the compound of Formula II and the compound of Formula IIA, with the exception of the recited groups of $W^5$, $W^6$, and $Y^4$, where in Formulas VIII and VIIIA one of $W^5$ and $W^6$ is $W^{16}$ or $Y^4$ is $Y^{12}$ and the remaining $W^5$ and $W^6$ (i.e., when not $W^{16}$) are each independently H and the remaining $Y^4$ (i.e., when not $Y^{12}$) is OH or $NH_2$;

(iii) an intermediate of Formula IX and an intermediate of Formula IXA that respectively correspond to the compound of Formula III and the compound of Formula IIIA, with the exception of the recited groups of $W^7$, $W^8$, and $Y^5$, where in Formulas IX and IXA one of $W^7$ and $W^5$ is $W^6$ or $Y^5$ is $Y^{12}$ and the remaining $W^7$ and $W^8$ (i.e., when not $W^{16}$) are each independently H and the remaining $Y^5$ (i.e., when not $Y^{12}$) is OH or $NH_2$;

(iv) an intermediate of Formula X and an intermediate of Formula XA that respectively correspond to the compound of Formula IV and the compound of Formula IVA, with the exception of the recited groups of $W^9$ and $W^{10}$, where in Formulas X and XA one of $W^9$ and $W^{10}$ is $W^{16}$ and the remaining $W^9$ and $W^{10}$ (i.e., when not $W^{16}$) is H;

(v) an intermediate of Formula XI and an intermediate of Formula XIA that respectively correspond to the compound of Formula V and the compound of Formula VA, with the exception of the recited groups of $W^{11}$, $W^{12}$, and $Y^6$, where in Formulas XI and XIA one of $W^{11}$ and $W^{12}$ is $W^{16}$ or $Y^6$ is $Y^{12}$ and the remaining $W^{11}$ and $W^{12}$ (i.e., when not $W^{16}$) are each independently H and the remaining $Y^6$ (i.e., when not $Y^{12}$) is OH or $NH_2$.

Similarly, an intermediate for producing a $^{18}F$-labeled bombesin receptor agonist of the present technology includes, but is not limited to, an intermediate that includes a bombesin receptor agonist with a primary amine, secondary amine, $NH_2$ of a guanadinyl group, or $NH_2$ of an amidinyl group of the bombesin receptor agonist covalently bonded to $W^{16}$ or a carboxylic acid or amide of the bombesin receptor agonist that is modified to a —$C(O)Y^{12}$ group. Exemplary intermediates include an intermediate of Formula X and an intermediate of Formula XA that respectively correspond to the compound of Formula VI and the compound of Formula VIA with the exception of the recited groups of $W^{13}$, $W^{14}$, $Y^7$, $Y^8$, $Y^9$, and $Y^{10}$, where in Formulas X and XA one of $W^{13}$ and $W^{14}$ is $W^{16}$ or one of $Y^7$, $Y^8$, $Y^9$, and $Y^{10}$ is $Y^{12}$ and the remaining $W^{13}$ and $W^{14}$ (i.e., when not $W^{16}$) are each independently H and the remaining $Y^7$, $Y^8$, $Y^9$, and $Y^{10}$ (i.e., when not $Y^{12}$) are each independently OH or $NH_2$.

The present technology also provides intermediates to the $^{18}F$-labeled seprase binding compounds, where such intermediates include a seprase binding compound with a primary amine, secondary amine, $NH_2$ of a guanadinyl group, or $NH_2$ of an amidinyl group of the seprase binding compound covalently bonded to $W^{16}$ or a carboxylic acid or amide of the seprase binding compound that is modified to a —$C(O)Y^{11}$ group.

For the above described exemplary intermediates, $W^{16}$ is independently at each occurrence

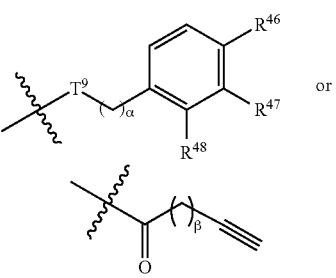

and
$Y^{12}$ is independently at each occurrence

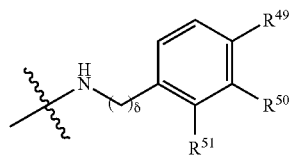

wherein $T^9$ is —C(O)— or —C(O)NH—, one of $R^{46}$, $R^{47}$, and $R^{48}$ and one of $R^{49}$, $R^{50}$, and $R^{51}$ is

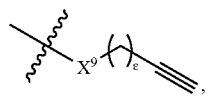

the remaining two of $R^{46}$, $R^{47}$, and $R^{48}$ are each H and the remaining two of $R^{49}$, $R^{50}$, and $R^{51}$ are each H; $X^9$ is absent, O, S, or NH; α and δ are each independently 0, 1, 2, or 3; e is 0, 1, 2, or 3, provided that when e is 0 then $X^9$ is absent; and β is 0, 1, 2, or 3.

In a related aspect, a method of forming a compound of any aspect and embodiment of an $^{18}F$-labeled peptide ligands is provided. The method includes contacting in the presence of a solvent a any aspect and embodiment of an intermediate as described herein, a copper salt, and an azide of Formula XX

(XX)

where χ is independently at each occurrence 1 or 2. The copper salt may be a copper (I) salt (such as copper (I) iodide), a copper (II) salt (such as copper (II) sulfate), or a mixture thereof. The solvent may be a protic solvent, and aprotic solvent, or a mixture thereof. Protic solvents as used herein include, but are not limited to, alcohols (e.g., methanol ($CH_3OH$), ethanol (EtOH), isopropanol (iPrOH), trifluoroethanol (TFE), butanol (BuOH), ethylene glycol, propylene glycol), carboxylic acids (e.g., formic acid, acetic acid, propanoic acid, butanoic acid, pentanoic acid, lauric acid, stearic acid, deoxycholic acid, glutamic acid, glucuronic acid), ammonia ($NH_3$), a primary amino compound (e.g., methyl amine, ethyl amine, propyl amine), a secondary amino compound (e.g., dimethyl amine, diethyl amine, di(n-propyl) amine), water, or a mixture of any two or more thereof. Polar aprotic solvents as used herein include, but are not limited to, ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), carbonates (e.g., ethylene carbonate, propylene carbonate, trimethylene carbonate), amides (e.g., dimethylformamide (DMF), dimethylacetamide (DMA)), nitriles (e.g., acetonitrile ($CH_3CN$), propionitrile ($CH_3CH_2CN$), benzonitrile (PhCN)), sulfoxides (e.g., dimethyl sulfoxide, also referred to as "DMSO"), sulfones (e.g., sulfolane), or a mixture of any two or more thereof. For example, the solvent may include DMF and DMSO.

In an aspect of the present technology, a composition is provided that includes any one of the aspects and embodiments of $^{18}$F-labeled peptide ligands of the present technology and a pharmaceutically acceptable carrier. As used herein, a "pharmaceutically acceptable carrier" includes carriers and/or excipients. In a related aspect, a pharmaceutical composition is provided, the pharmaceutical composition including an effective amount of the compound of any one of the aspects and embodiments of a $^{18}$F-labeled peptide ligand of the present technology for imaging a condition; and where the condition includes a mammalian tissue expressing (e.g., overexpressing) a somatostatin receptor (e.g., one or more of SSTR1, SSTR2, SSTR3, SSTR4, and SSTR5), a bombesin receptor (e.g., one or more of BBR1, BBR2, and BBR3), seprase, or a combination of any two or more thereof. Exemplary conditions that include somatostatin receptor expression include, but are not limited to, growth hormone producing tumors, neuroendocrine tumors, pituitary tumors (e.g., that secrete thyroid stimulating hormone), neuroendocrine tumors, carcinoid syndrome, vasoactive intestinal peptide-secreting tumors, Cushing's disease, acromegaly, cirrhotic liver disease, and AIDS-related diarrhea. Exemplary conditions that include bombesin receptor expression include, but are not limited to, small cell carcinoma of the lung, gastric cancer, pancreatic cancer, and neuroblastoma. Exemplary conditions that include seprase expression include a variety of metastatic cancers. In a further related aspect, an imaging method is provided that includes administering a compound of any one of the aspects and embodiments of a $^{18}$F-labeled peptide ligand of the present technology (e.g., such as administering an effective amount) or administering a pharmaceutical composition comprising an effective amount of a compound of any one of the aspects and embodiments of a $^{18}$F-labeled peptide ligand of the present technology to a subject and, subsequent to the administering, detecting positron emission, detecting gamma rays from positron emission and annihilation (such as by positron emission tomography), and/or detecting Cerenkov radiation due to positron emission (such as by Cerenkov luminescene imaging). In any embodiment of the imaging method, the subject may be suspected of suffering from a condition that includes amammalian tissue expressing (e.g., overexpressing) a somatostatin receptor (e.g., one or more of SSTR1, SSTR2, SSTR3, SSTR4, and SSTR5), a bombesin receptor (e.g., one or more of BBR1, BBR2, and BBR3), seprase, or a combination of any two or more thereof, where exemplary conditions are provided supra. The detecting step may occur during a surgical procedure on a subject, e.g., to remove amammalian tissue imaged via the method. The detecting step may include use of a handheld device to perform the detecting step. For example, Cerenkov luminescene images may be acquired by detecting the Cerenkov light using ultra-high-sensitivity optical cameras such as electron-multiplying charge-coupled device (EMCCD) cameras.

"Effective amount" refers to the amount of a compound or composition required to produce a desired effect, such as a quantity of a compound of the present technology necessary to be detected by the detection method chosen. For example, an effective amount of a compound of the present technology includes an amount sufficient to enable detection of binding of the compound to a target of interest including, but not limited to, one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer. Another example of an effective amount includes amounts or dosages that are capable of providing a detectable gamma ray emission from positron emission and annihilation (above background) in a subject with a tissue expressing (e.g., overexpressing) a somatostatin receptor (e.g., one or more of SSTR1, SSTR2, SSTR3, SSTR4, and SSTR5), a bombesin receptor (e.g., one or more of BBR1, BBR2, and BBR3), seprase, or a combination of any two or more thereof, such as, for example, statistically significant emission above background. Another example of an effective amount includes amounts or dosages that are capable of providing a detectable Cerenkov radiation emission due to positron emission (above background) in a subject with a tissue expressing (e.g., overexpressing) a somatostatin receptor, a bombesin receptor, seprase, or a combination of any two or more thereof, such as, for example, statistically significant emission above background. As used herein, a "subject" or "patient" is a mammal, such as a cat, dog, rodent or primate. Typically the subject is a human, and, preferably, a human suffering from or suspected of suffering from a condition that includes a mammalian tissue expressing (e.g., overexpressing) a somatostatin receptor, a bombesin receptor, seprase, or a combination of any two or more thereof, such as one or more of a growth hormone producing tumor, a neuroendocrine tumor, a pituitary tumors, a vasoactive intestinal peptide-secreting tumor, a small cell carcinoma of the lung, gastric cancer tissue, pancreatic cancer tissue, a neuroblastoma, and a metastatic cancer. The term "subject" and "patient" may be used interchangeably.

The instant present technology provides pharmaceutical compositions and medicaments comprising any one or more of the $^{18}$F-labeled peptide ligands of any embodiment disclosed herein (e.g., $^{18}$F-labeled somatostatin receptor agonist, $^{18}$F-labeled bombesin receptor agonist, $^{18}$F-labeled seprase binding compound, a compound of any embodiment of any one or more of Formulas I, IA, IB, II, IIA, III, IIIA, IV, IVA, V, VA, VI, and VIA) and a pharmaceutically acceptable carrier or one or more excipients or fillers (collectively, such carriers, excipients, fillers, etc., will be referred to as "pharmaceutically acceptable carriers" unless a more specific term is used). The compositions may be used in the methods and imagings described herein. Such compositions and medicaments include an effective amount of any $^{18}$F-labeled peptide ligand as described herein (e.g., $^{18}$F-labeled somatostatin receptor agonist, $^{18}$F-labeled bombesin receptor agonist, $^{18}$F-labeled seprase binding compound, a compound of any embodiment of any one or more of Formulas I, IA, IB, II, IIA, III, IIIA, IV, IVA, V, VA, VI, and VIA), for imaging one or more of the herein-described conditions. The pharmaceutical composition may be packaged in unit dosage form. For example, the unit dosage form is effective in imaging a mammalian tissue expressing (e.g., overexpressing) a somatostatin receptor, a bombesin receptor, seprase, or a combination of any two or more thereof, when administered to a subject. Such mammalian tissue may include one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to image disorders associated with a mammalian tissue expressing (e.g., overexpressing) a somatostatin receptor, a bombesin receptor, seprase, or a combination of any two or more thereof, when administered to a subject. Such mammalian tissue may include one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer. The compounds and compositions described herein may be used to prepare formulations and medicaments for imaging a variety of disorders associated with such mammalian tissue. Such compositions can be in the form of, for example, granules, powders, tablets, capsules, syrup, suppositories, injections, emulsions, elixirs, suspensions or solutions. The instant compositions can be formulated for various routes of administration, for example, by parenteral or systemic administration. Parenteral or systemic administration includes, but is not limited to, subcutaneous, intravenous, intraperitoneal, and intramuscular, injections. The following dosage forms are given by way of example and should not be construed as limiting the instant present technology.

Liquid dosage forms for administration may be in the form of pharmaceutically acceptable emulsions, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. An isotonic solution will be understood as isotonic with the subject. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The instant compositions may also comprise, for example, micelles or liposomes, or some other encapsulated form, or may be administered in an extended release form to provide a prolonged storage and/or delivery effect.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, statistically significant resolution (via, e.g., positron emission tomography or Cerenkov luminescence imaging) is achieved of a mammalian tissue that expressing (e.g., overexpressing) a somatostatin receptor, a bombesin receptor, seprase, or a combination of any two or more thereof, when administered to a subject. Such mammalian tissue may include one or more of a growth hormone producing tumor, a neuroendocrine tumor, a pituitary tumors, a vasoactive intestinal peptide-secreting tumor, a small cell carcinoma of the lung, gastric cancer tissue, pancreatic cancer tissue, a neuroblastoma, and a metastatic cancer. The compounds of the present technology may be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being imaged and the pharmacological activity of the compound being used. The determination of optimum dosages for a particular patient is well known to those skilled in the art. Various assays and model systems can be readily employed to determine the effectiveness of a compound according to the present technology.

The compounds of the present technology can also be administered to a patient along with other conventional imaging agents that may be useful in the imaging of a mammalian tissue expressing (e.g., overexpressing) a somatostatin receptor, a bombesin receptor, seprase, or a combination of any two or more thereof, when administered to a subject. Such mammalian tissue may include one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer. Thus, a pharmaceutical composition of the present technology may further include an imaging agent different than a $^{18}$F-labeled peptide ligand of the present technology. The administration may include parenteral administration. In any of these embodiments, the administration may include subcutaneous injections, intravenous injections, intraperitoneal injections, or intramuscular injections. The methods of the present technology may also include administering, either sequentially or in combination with one or more compounds of the present technology, a conventional imaging agent in an amount that can potentially or synergistically be effective for the imaging of a mammalian tissue expressing (e.g., overexpressing) a somatostatin receptor, a bombesin receptor, seprase, or a combination of any two or more thereof, when administered to a subject.

In an aspect, a compound of the present technology is administered to a patient in an amount or dosage suitable for imaging. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

Synthesis of $^{18}$F-Labeled Peptide Ligands of the Present Technology

The peptides of the $^{18}$F-labeled peptide ligands of the present technology may be synthesized by any method known in the art. Exemplary, non-limiting methods for chemically synthesizing peptides include those described by Stuart and Young in "*Solid Phase Peptide Synthesis*," Second Edition, Pierce Chemical Company (1984), and in "*Solid Phase Peptide Synthesis*," Methods Enzymol. 289, Academic Press, Inc, New York (1997). Furthermore, recombinant peptides may be generated using conventional techniques in molecular biology, protein biochemistry, cell biology, and microbiology, such as those described in *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, NY, 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, Meth. Enzymol., (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

Synthesis of $^{18}$F-labeled peptide ligands of the present technology from peptides are also readily understood by one of ordinary skill in the art, including in view of the present disclosure, where exemplary protocols for synthesis of $^{18}$F-labeled peptide ligands of the present technology include protocols similar to those described in International Appl. No. PCT/US2017/039710, incorporated herein by reference and wherein a more detailed discussion of the working examples of International Appl. No. PCT/US2017/039710 is provided below.

Synthesis and Examples Provided in Int'l Appl. No. PCT/US2017/039710

For the working examples of International Appl. No. PCT/US2017/039710, all solvents were purchased from Sigma Aldrich and were of reagent grade quality unless otherwise indicated. Solvents were dried either by distillation over an activated stainless steel column (Pure Process Technology, LLC) column or by drying over activated molecular sieves. Reagents were purchased from Sigma Aldrich, Alfa Aesar, Combi Blocks, ChemBridge and Enamine, and were of reagent grade with the exception of 3-(prop-2-yn-1-yloxy)aniline (Enamine), which was 80-85% pure by HPLC.

All reactions were carried out in dried glassware. Purifications were performed using silica chromatography on VWR® High Purity Silica Gel 60 Å. Preparative HPLC was performed using an XBridge™ Prep C18 5 μm OBD™ 19×100 mm column (Waters) on a dual pump Agilent ProStar HPLC fitted with an Agilent ProStar 325 Dual Wavelength UV-Vis Detector. UV absorption was monitored at 220 nm and 280 nm. A binary solvent system was used, with solvent A comprising $H_2O$+0.01% TFA and solvent B consisting of 90% v/v MeCN/$H_2O$+0.01% TFA. Purification was achieved using the following gradient HPLC method: 0% B 0-1 min., 0-100% B 1-28 mins., 100-0% B 28-30 mins.

Final products were identified and characterized using thin layer chromatography, analytical HPLC, mass spectroscopy and NMR spectroscopy. Analytical HPLC was performed using an XSelect™ CSH™ C18 5 μm 4.6×50 mm column (Waters). Mass determinations were performed by LCMS analysis using a Waters ACQUITY UPLC@coupled to a Waters SQ Detector 2. NMR analyses were performed using a Bruker Avance III 500 MHz spectrometer. Spectra are reported as ppm and are referenced to the solvent resonances in DMSO-d6 or chloroform-d (Sigma Aldrich). The purity of all compounds evaluated in the biological assay was >95% purity as judged by LC-MS and 1H NMR.

Representative Synthesis of Intermediates of Int'l Appl. No. PCT/US2017/039710

Representative synthetic procedures (Routes A & B) are provided below in Scheme 2 for generating exemplary intermediates of Int'l Appl. No. PCT/US2017/039710.

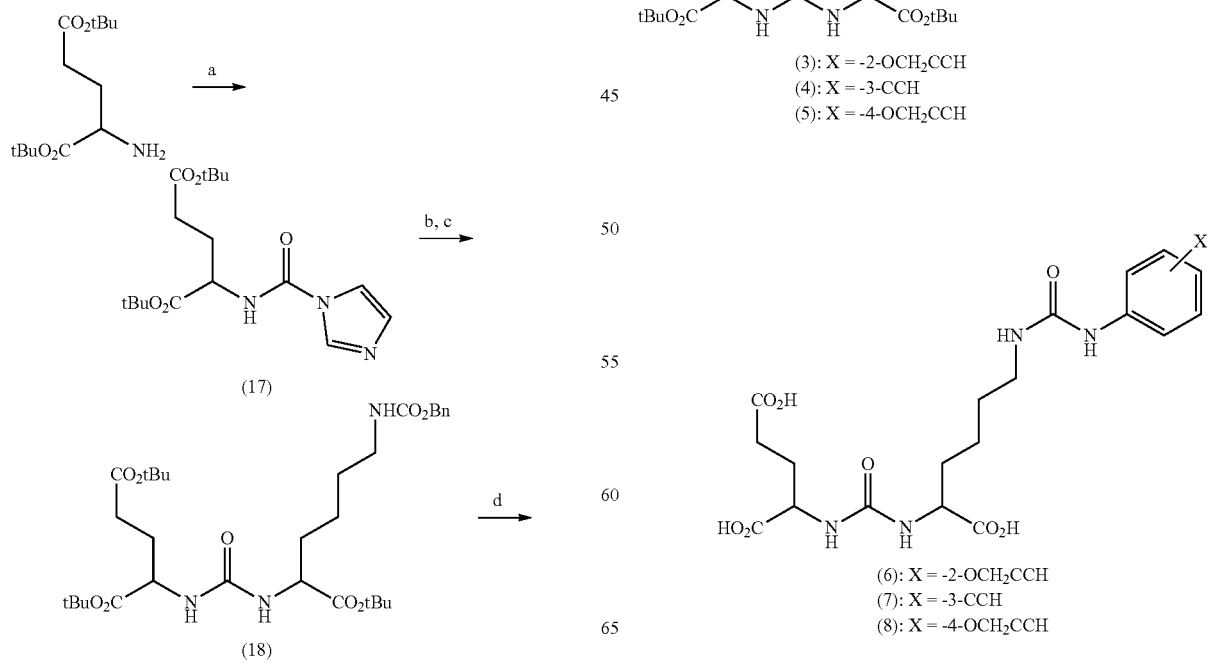

39
Route B (1) →<sup>i</sup>

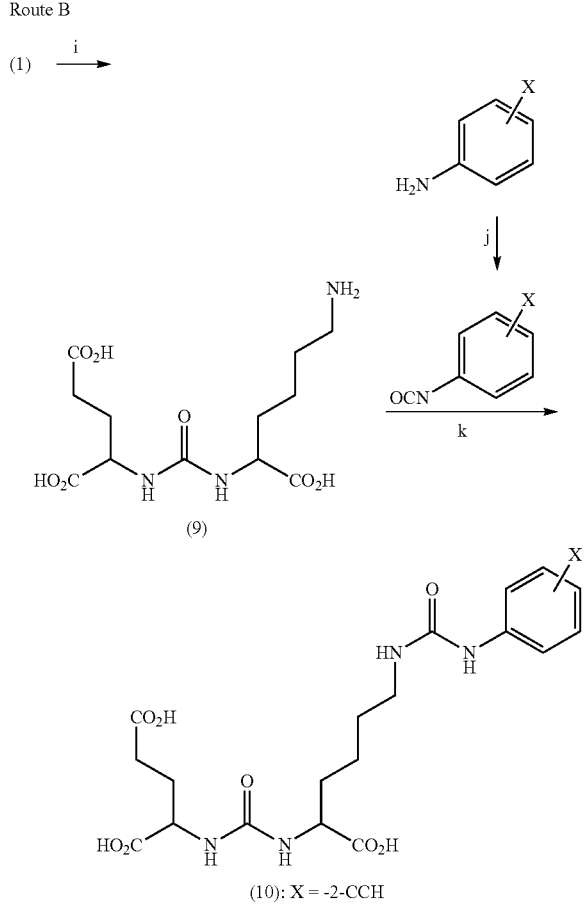

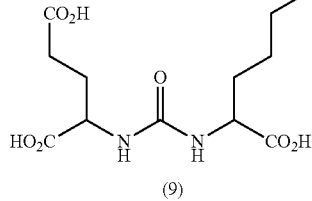

(10): X = -2-CCH
(11): X = -3-OCH₂CCH
(12): X = -4-CCH a. DMAP, CDI, NEt₃, 0° C.; b. MeOTf, NEt₃, 0° C.; c. H₂N-Lys(Cbz)-OtBu; d. H₂, Pd/C; e. DMAP, CDI, NEt₃; f. MeOTf, NEt₃, 0° C.; g. 2- or 4-(2-propyn-1-yloxy)aniline or 3-ethynylaniline, rt; h. TFA/CH₂Cl₂; i. TFA/CH₂Cl₂; j. triphosgene, NEt₃, reflux; k. NEt₃, rt.

The synthesis of exemplary intermediates via Route A and Route B are provided below.

Di-tert-butyl (1H-imidazole-1-carbonyl)-L-glutamate (17)

The hydrochloride salt of L-H-Glu(OtBu)-OtBu (1.25 g, 4.23 mmol) was dissolved in $CH_2Cl_2$ (30 mL) with a catalytic amount of N,N'-dimethylaminopyridine (50 mg), and the solution was cooled to 0° C. and stirred under Ar. Triethylamine (4.5 mL) was added followed by 1,1'-carbonyldiimidazole (754 mg, 4.65 mmol), and the resulting mixture was stirred overnight with warming to room temperature. The reaction was then diluted with $CH_2Cl_2$ and washed successively with $H_2O$ and saturated NaCl solution. The organic layer was dried over $MgSO_4$, filtered and concentrated under reduced pressure to give an oil that solidified upon standing. The crude product was purified by silica chromatography (0-100% MeOH in EtOAc) to give the product, di-tert-butyl (1H-imidazole-1-carbonyl)-L-glutamate (17), as a transparent oil (1.00 g, 61% yield). $^1$H NMR (500 MHz, $CDCl_3$) δ 8.18 (s, 1H), 7.48 (d, 1H, J=6.2 Hz), 7.42 (s, 1H), 7.10 (s, 1H), 4.45 (m, 1H), 2.44 (m, 2H), 2.18 (m, 2H), 1.50 (s, 9H), 1.46 (s, 9H).

40
Tri-tert-butyl (9S,13S)-3,11-dioxo-1-phenyl-2-oxa-4,10,12-triazapentadecane-9,13,15-tricarboxylate (18)

A solution of di-tert-butyl (1H-imidazole-1-carbonyl)-L-glutamate (17) (572 mg, 1.48 mmol) in dichloroethane (6 mL) was cooled to 0° C. and stirred under Ar. A solution of trimethylamine (0.42 mL, 3.0 mmol) in dichloroethane (1 mL) was added followed by a solution of methyl triflate (160 μL, 1.5 mmol) in dichloroethane. The reaction was stirred for 60 min, warming to room temperature. Then a solution of L-H-Lys(Cbz)-OtBu.HCl (552 mg, 1.48 mmol) in dichloroethane (10 mL) was added, and the reaction was stirred for 6 h at 50° C. under Ar. The mixture was then cooled to room temperature and concentrated under reduced pressure to give an oil. The oil was purified by silica chromatography (20% EtOAC in hexanes to 50% EtOAc in hexanes) to give the product, tri-tert-butyl (9S,13S)-3,11-dioxo-1-phenyl-2-oxa-4,10,12-triazapentadecane-9,13,15-tricarboxylate (18), as a transparent oil (678 mg, 74% yield).

Di-tert-butyl (((S)-6-amino-1-(tert-butyloxy)-1-oxohexan-2-yl)carbamoyl)-L-glutamate (1)

Activated palladium on carbon (0.1 eq) was suspended in a solution of tri-tert-butyl (9S,13S)-3,11-dioxo-1-phenyl-2-oxa-4,10,12-triazapentadecane-9,13,15-tricarboxylate (18) (500 mg) in EtOH (15 mL). The suspension was stirred overnight at room temperature under $H_2$ atmosphere. The mixture was then filtered through celite, and the filtrate was concentrated under reduced pressure to give the product, di-tert-butyl (((S)-6-amino-1-(tert-butyoxy)-1-oxohexan-2-yl)carbamoyl)-L-glutamate (1) as a viscous oil (360 mg, 92% yield).

Route A Synthesis

Di-tert-butyl (((S)-1-(tert-butoxy)-6-(1H-imidazole-1-carboxamido)-1-oxohexan-2-yl)carbamoyl)-L-glutamate (2)

Compound 1 (1.46 g, 3.0 mmol) was dissolved in dichloroethane (10 mL) with triethylamine (0.84 mL, 6.0 mmol) and a catalytic amount of N,N'-dimethylaminopyridine (15 mg) and stirred at room temperature under Ar. After 5 min, a suspension of 1,1'-carbonyldiimidazole (486 mg, 3.3 mmol) in dichloroethane (2 mL) was added, and the reaction was stirred overnight under Ar. The solution was then washed successively with 1% v/v AcOH in $H_2O$ and saturated NaCl solution. The organic layer was dried over $MgSO_4$, filtered and concentrated under reduced pressure to give a yellow oil. The oil was purified by silica chromatography (50% EtOAc in hexanes to 10% MeOH in EtOAc) to give the product, di-tert-butyl (((S)-1-(tert-butoxy)-6-(1H-imidazole-1-carboxamido)-1-oxohexan-2-yl)carbamoyl)-L-glutamate (2), as an off white powder (60% yield). $^1$H NMR (500 MHz, $CDCl_3$) δ 8.34 (s, 1H), 7.94 (br s, 1H), 7.69 (s, 1H), 7.05 (s, 1H), 5.95 (d, 1H, J=7.8 Hz), 5.58 (d, 1H, J=7.6 Hz), 4.21 (m, 1H), 4.16 (m, 1H), 3.53 (m, 1H), 3.28 (m, 1H), 2.30 (m, 2H), 2.05 (m, 1H), 1.83 (m, 1H), 1.79 (m, 1H), 1.72 (m, 1H), 1.50 (m, 2H), 1.43 (s, 18H), 1.38 (s, 9H), 1.32 (m, 2H). ESI(+)=582.5 (M+H)+. Calculated mass: 581.34

Di-tert-butyl (((S)-1-(ter-butoxy)-1-oxo-6-(3-(2-prop-2-yn-1-yloxy)phenyl)ureido)hexan-2-yl)carbamoyl)-L-glutamate (3)

A solution of di-tert-butyl (((S)-1-(tert-butoxy)-6-(1H-imidazole-1-carboxamido)-1-oxohexan-2-yl)carbamoyl)-L- glutamate (2) (182 mg, 0.30 mmol) in dichloroethane (4 mL) was cooled to 0° C. and stirred under Ar. A solution of triethylamine (87 µL, 0.63 mmol) in dichloroethane (1 mL) was added followed by a solution of methyl triflate (34 uL, 0.31 mmol) in dichloroethane (1 mL).

The reaction was stirred for 60 min, warming to room temperature. Then 2 mL of the reaction mixture was transferred under Ar to a round-bottom flask containing a solution of 2-(2-propyn-1-yloxy)aniline (15 mg, 0.10 mmol) in dichloroethane (1 mL). The resulting mixture was stirred at room temperature for 16 h under Ar. The mixture was then cooled to room temperature and concentrated under reduced pressure to give an oil. The oil was purified by reverse phase prep HPLC (12 mL/min, 0% B to 100% B over 30 min followed by 5 min at 100% B; λ=220 nm, 254 nm). The peak containing the product was lyophilized and the product, di-tert-butyl (((S)-1-(tert-butoxy)-1-oxo-6-(3-(2-prop-2-yn-1-yloxy)phenyl)ureido)hexan-2-yl)carbamoyl)-L-glutamate (3), was isolated as a white powder (28 mg, 45% yield). $^1$H NMR (500 MHz, CDCl$_3$) δ 8.20 (d, 1H, J=7.8 Hz), 7.45 (br s, 1H), 6.97 (m, 1H), 6.84 (m, 2H), 6.71 (m, 2H), 6.00 (br s, 1H), 5.69 (br s, 1H), 5.50 (d, 1H, J=7.0 Hz), 4.67 (dd, 2H, J$_1$=7.2 Hz, J$_2$=2.4 Hz), 4.36 (m, 1H), 4.21 (m, 1H), 3.12 (m, 2H), 2.54 (t, 1H, J=2.4 Hz), 2.33 (m, 2H), 2.03 (m, 1H), 1.87 (m, 1H), 1.75 (m, 1H), 1.54-1.38 (m, 5H), 1.41 (s, 18H), 1.37 (s, 9H). ESI(+)=661.5 (M+H)+. Calculated mass: 660.37

Di-tert-butyl (((S)-1-(ter-butoxy)-6-(3-(2-ethynylphenyl)ureido)-1-oxohexan-2-yl)carbamoyl)-L-glutamate (4)

The compound was synthesized by the same method from 3-ethynyl aniline (1.1 eq) and urea (2) (1.0 eq) and isolated as an orange semi-solid (33%). $^1$H NMR (500 MHz, CDCl$_3$) δ 7.90 (s, 1H), 7.58 (t, 1H, J=1.7 Hz), 7.51 (dd, 1H, J$_1$=8.2 Hz, J$_2$=1.3 Hz), 7.18 (t, 1H, J=7.9 Hz), 7.05 (d, 1H, J=7.7 Hz), 6.38 (d, 1H, J=7.9 Hz), 6.28 (br s, 1H), 5.77 (d, 1H, J=6.9 Hz), 4.32 (m, 1H), 4.02 (m, 1H), 3.53 (m, 1H), 3.05 (m, 1H), 3.00 (s, 1H), 2.39 (m, 2H), 2.07 (m, 1H), 1.88 (m, 1H), 1.74 (m, 1H), 1.62 (m, 1H), 1.49-1.37 (m, 4H), 1.41 (s, 18H), 1.37 (s, 9H). ESI(+)=631.5 (M+H)+. Calculated mass: 630.36

Di-tert-butyl (((S)-1-(tert-butoxy)-1-oxo-6-(3-(4-prop-2-yn-1-yloxy)phenyl)ureido)hexan-2-yl)carbamoyl)-L-glutamate (5)

The compound was synthesized by the same method from [4-(2-propyn-1-yloxy)phenyl]amine hydrochloride (1.1 eq) and urea (2) (1.0 eq) and isolated as a light brown oil (46%). H NMR (500 MHz, CDCl$_3$) δ 7.60 (s, 1H), 7.33 (d, 2H, J=9.0 Hz), 6.86 (d, 2H, J=9.0 Hz), 6.24 (d, 1H, J=7.8 Hz), 6.05 (br s, 1H), 5.71 (d, 1H, J=7.0 Hz), 4.61 (d, 2H, J=2.3 Hz), 4.30 (m, 1H), 4.03 (m, 1H), 3.45 (m, 1H), 3.05 (m, 1H), 2.47 (t, 1H, J=2.3 Hz), 2.31 (m, 2H), 2.06 (m, 1H), 1.83 (m, 1H), 1.75 (m, 1H), 1.48 (m, 3H), 1.41 (s, 9H), 1.39 (s, 9H), 1.37 (s, 9H), 1.31 (m, 2H). ESI(+)=661.4 (M+H)+. Calculated mass: 660.37

(((S)-1-Carboxy-5-(3-(2-(prop-2-yn-1-yloxy)phenyl)ureido)pentyl)carbamoyl)-L-glutamic acid (6)

Di-tert-butyl (((S)-1-(tert-butoxy)-1-oxo-6-(3-(2-prop-2-yn-1-yloxy)phenyl)ureido)hexan-2-yl)carbamoyl)-L-glutamate (3) (4.2 mg, 6.4 µmol) was dissolved in CH$_2$Cl$_2$ (0.5 mL). Trifluoroacetic acid (0.5 mL) was added, and the mixture was stirred overnight at room temperature. The volatile solvents were removed under a stream of N2, and the resulting crude residue was lyophilized to give the product, (((S)-1-carboxy-5-(3-(2-(prop-2-yn-1-yloxy)phenyl)ureido)pentyl)carbamoyl)-L-glutamic acid (6) as a white powder (3.1 mg, 98% yield). $^1$H NMR (500 MHz, DMSO-d6) δ 8.10 (m, 1H), 7.83 (s, 1H), 7.03 (m, 1H), 6.90 (br s, 1H), 6.86 (m, 2H), 6.33 (d, 1H, J=12.5 Hz), 6.31 (d, 1H, J=12.5 Hz), 4.86 (d, 2H, J=2.3 Hz), 4.10 (m, 2H), 3.60 (t, 1H, J=2.3 Hz), 3.06 (m, 2H), 2.24 (m, 2H), 1.93 (m, 1H), 1.69 (m, 2H), 1.56 (m, 1H), 1.42 (m, 2H), 1.32 (m, 2H). ESI(+)=493.3 (M+H)+. Calculated mass: 492.19

(((S)-1-carboxy-5-(3-(3-ethynylphenyl)ureido)pentyl)carbamoyl)-L-glutamic acid (7)

Alkyne (4) was deprotected by the same method and the title compound was isolated as a white powder (61%). $^1$H NMR (500 MHz, DMSO-d6) δ 8.42 (s, 1H), 7.11 (m, 2H), 6.91 (d, 1H, J=8.2 Hz), 6.50 (dd, 1H, J$_1$=8.2 Hz, J$_2$=2.4 Hz), 6.31 (m, 2H), 6.13 (br s, 1H), 4.71 (d, 2H, J=2.2 Hz), 4.08 (m, 2H), 3.05 (m, 2H), 2.24 (m, 2H), 1.91 (m, 1H), 1.70 (m, 2H), 1.54 (m, 1H), 1.41 (m, 2H), 1.30 (m, 2H). ESI(+)=463.3 (M+H)+. Calculated mass: 462.18

((1-Carboxy-5-(3-(4-(prop-2-yn-1-yloxy)phenyl)ureido)pentyl)carbamoyl)glutamic acid (8)

Alkyne (5) was deprotected by the same method and title compound was isolated as a white powder (96%). $^1$H NMR (500 MHz, DMSO-d6) δ 8.28 (s, 1H), 7.31 (d, 2H, J=9.0 Hz), 6.87 (d, 2H, J=9.0 Hz), 6.35 (d, 1H, J=11.4 Hz), 6.34 (d, 1H, J=11.4 Hz), 6.09 (br s, 1H), 4.72 (d, 2H, J=2.3 Hz), 4.10 (m, 2H), 3.54 (t, 1H, J=2.3 Hz), 3.06 (m, 2H), 2.25 (m, 2H), 1.93 (m, 1H), 1.63 (m, 2H), 1.53 (m, 1H), 1.42 (m, 2H), 1.31 (m, 2H). ESI(+)=493.3 (M+H)+. Calculated mass: 492.19

Route B Synthesis

(((S)-5-Amino-1-carboxypentyl)carbamoyl)-L-glutamic acid (9)

Compound (1) (1.22 g, 2.5 mmol) was dissolved in CH$_2$Cl$_2$ (5 mL). Trifluoroacetic acid (1.5 mL) was added, and the reaction was stirred overnight at room temperature. The volatile materials were removed under a stream of N$_2$, and the crude product was lyophilized to give (((S)-amino-1-carboxypentyl)carbamoyl)-L-glutamic acid (9) as a viscous oil (700 mg, 88%). $^1$H NMR (500 MHz, DMSO-d6) δ 7.71 (s, 2H), 6.37 (m, 2H), 4.08 (m, 2H), 2.78 (m, 2H), 2.25 (m, 2H), 1.93 (m, 1H), 1.70 (m, 2H), 1.53 (m, 3H), 1.32 (m, 2H).

(((S)-1-Carboxy-5-(3-(2-ethynylphenyl)ureido)pentyl)carbamoyl)-L-glutamic acid (10)

A solution of 2-ethynyl aniline (30 µL, 0.26 mmol) in toluene (1 mL) was added slowly to a solution of triphosgene (56 mg, 0.19 mmol) in toluene (3 mL) at room temperature under Ar. Triethylamine (42 µL, 0.30 mmol) was added and the reaction was heated to reflux for 6 h. The solvent was removed under reduced pressure, and the crude residue, a yellow/white semisolid, was dissolved in DMF (2 mL). Then a solution of amine (9) (60 mg, 0.19 mmol) in DMF (1 mL) was added, followed by triethylamine (42 µL, 0.30 mmol). The reaction was stirred at room temperature for 90 min. The mixture was concentrated under reduced pressure and the crude residue was purified by reverse phase prep HPLC (12 mL/min, 0% B to 100% B over 30 min followed by 5 min at 100% B; λ=220 nm, 254 nm). The peak containing the product was collected and lyophilized to give (((S)-1-carboxy-5-(3-(2-ethynylphenyl)ureido)pentyl)carbamoyl)-L-glutamic acid (10) as a white powder (27 mg, 31% yield). $^1$H NMR (500 MHz, DMSO-d6) δ 8.13 (d, 1H, J=8.5 Hz), 7.86 (s, 1H), 7.37 (dd, 1H, $J_1$=7.6 Hz, $J_2$=1.3 Hz), 7.27 (m, 1H), 7.23 (br s, 1H), 6.90 (t, 1H, J=7.6 Hz), 6.34 (m, 2H), 4.56 (s, 1H), 4.10 (m, 2H), 3.08 (m, 2H), 2.25 (m, 2H), 1.93 (m, 1H), 1.70 (m, 2H), 1.57 (m, 1H), 1.44 (m, 2H), 1.33 (m, 2H). ESI(+)=463.5 (M+H)$^+$; ESI(−)=461.2 (M−H)$^−$. Calculated mass: 462.18

((1-Carboxy-5-(3-(3-(prop-2-yn-1-yloxy)phenyl)ureido)pentyl)carbamoyl) glutamic acid (11)

The compound was synthesized by the same method from amine (9) and 3-(prop-2-yn-1-yloxy)aniline and isolated as a light brown powder (13%). $^1$H NMR (500 MHz, DMSO-d6) δ 8.54 (s, 1H), 7.61 (s, 1H), 7.32 (dd, 1H, $J_1$=8.1 Hz, $J_2$=1.3 Hz), 7.21 (t, 1H, J=7.8 Hz), 6.98 (d, 1H, J=7.6 Hz), 6.33 (m, 2H), 6.21 (br s, 1H), 4.11 (s, 2H), 4.08 (m, 2H), 3.06 (m, 2H), 2.24 (m, 2H), 1.93 (m, 1H), 1.71 (m, 2H), 1.55 (m, 1H), 1.43 (m, 2H), 1.31 (m, 2H). ESI(+)=493.1 (M+H)+. Calculated mass: 492.19

(((S)-1-carboxy-5-(3-(4-ethynylphenyl)ureido)pentyl)carbamoyl)-L-glutamic acid (12)

The compound was synthesized by the same method from amine (9) and 4-ethynyl aniline and isolated as a pale green powder (38%). $^1$H NMR (500 MHz, DMSO-d6) δ 8.64 (s, 1H), 7.40 (d, 2H, J=8.5 Hz), 7.32 (d, 2H, J=8.5 Hz), 6.33 (m, 2H), 6.22 (br s, 1H), 4.10 (m, 2H), 3.99 (s, 1H), 3.07 (m, 2H), 2.25 (m, 2H), 1.93 (m, 1H), 1.70 (m, 2H), 1.55 (m, 1H), 1.43 (m, 2H), 1.31 (m, 2H). ESI(+)=463.4 (M+H)*; ESI(−)=461.3 (M−H)$^−$. Calculated mass: 462.18

Representative $^{18}$F Compounds of Int'l Appl. No. PCT/US2017/039710 from the Representative Intermediates Representative synthetic procedures are provided below in Scheme 3 in generating exemplary $^{19}$F compounds illustrative of $^{18}$F compounds of Int'l Appl. No. PCT/US2017/039710, followed by a more detailed description of the synthesis of these exemplary $^{19}$F compounds.

Scheme 3.

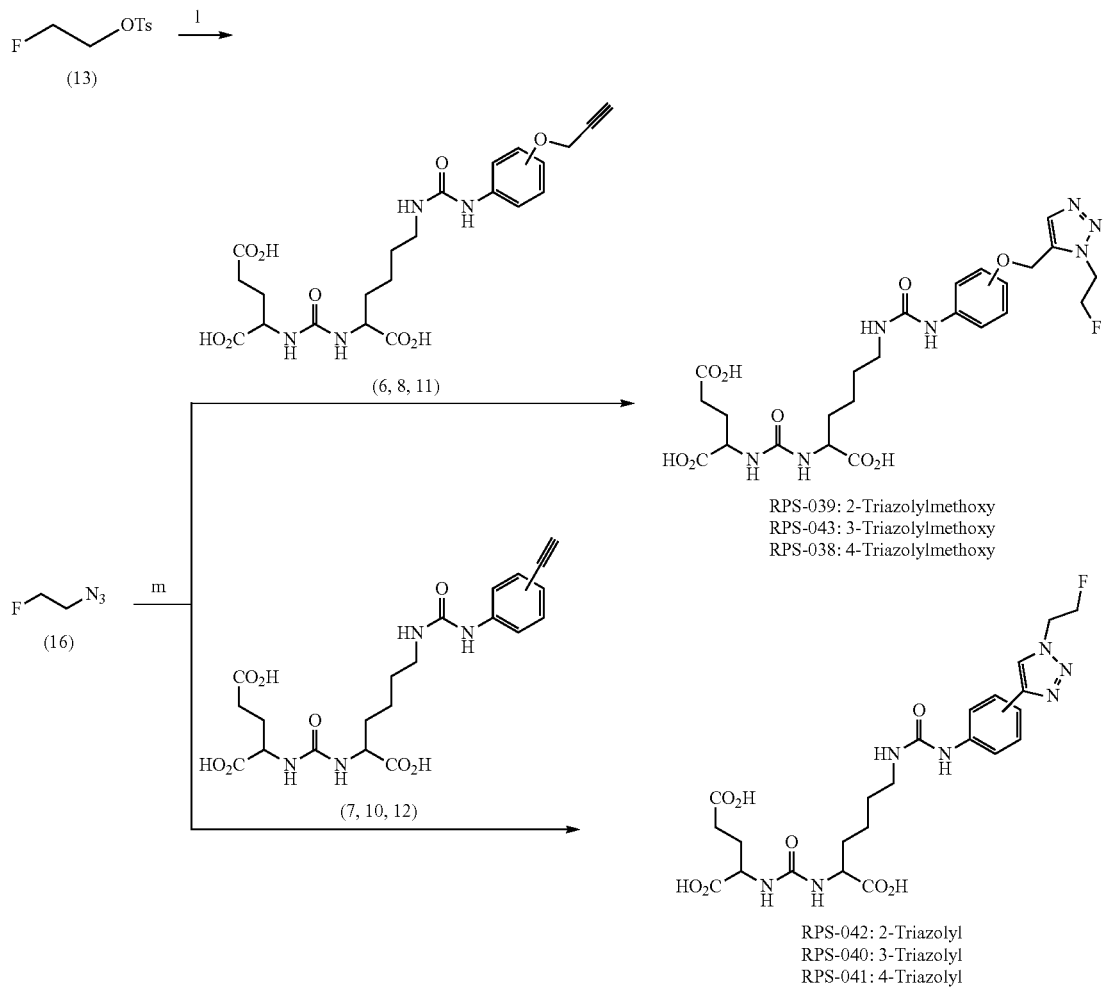

2-Fluoroethyltosylate (13)

A solution of tetrabutylammonium fluoride (2.2 mL, 1.0M in THF) was added to a suspension of di(p-toluenesulfonyl) ethanediol (740 mg, 2.0 mmol) in THF (15 mL), and the mixture was heated to reflux under Ar overnight. Then the reaction was cooled to room temperature and the solvent was removed under reduced pressure. The crude residue was partitioned between $H_2O$ and EtOAc. The layers were separated and the aqueous layer was extracted with EtOAc. The organic layers were combined and dried over $MgSO_4$, filtered and concentrated under reduced pressure to give a colorless oil. The oil was purified by silica chromatography (20% EtOAc in hexanes) to give 2-fluoroethyltosylate (13) as a colorless oil (225 mg, 52% yield). $^1$H NMR (500 MHz, $CDCl_3$) δ 7.79 (d, 2H, J=8.5 Hz), 7.35 (d, 2H, J=8.6 Hz), 4.61 (m, 1H), 4.51 (m, 1H), 4.28 (m, 1H), 4.22 (m, 1H), 2.45 (s, 3H).

(((S)-1-Carboxy-5-(3-(2-(1-(2-fluoroethyl)-1H-1,2,3-triazol-4-yl)phenyl)ureido)pentyl)carbamoyl)-L-glutamic acid (RPS-042)

Sodium azide (10 mg, 150 µmol) was suspended in a solution of 2-fluoroethyltosylate (7.5 mg, 30 µmol) in DMF (0.3 mL). The suspension was stirred overnight at room temperature and then filtered. To the filtrate was added a solution of alkyne (6) (0.9 mg, 1.83 µmol) in DMSO (0.2 mL). In a separate vial, 0.5M $CuSO_4$ (100 µL) and 1.5M sodium ascorbate (100 µL) were mixed for 5 min and then transferred to the reaction vial as a solution in DMF (100 µL). The reaction was stirred for 60 min at room temperature and was then purified by reverse phase prep HPLC (12 mL/min, 0% B to 100% B over 30 min followed by 5 min at 100% B; λ=220 nm, 254 nm). The peak containing the product was lyophilized, and RPS-042 was isolated as a white powder (0.8 mg, 75% yield). $^1$H NMR (500 MHz, DMSO-d6) δ 8.64 (s, 1H), 8.16 (d, 1H, J=8.1 Hz), 7.61 (d, 1H, J=7.8 Hz), 7.26 (dd, 1H, $J_1$=8.3 Hz, $J_2$=7.3 Hz), 7.12 (br s, 1H), 7.02 (m, 2H), 6.33 (d, 1H, J=8.3 Hz), 6.31 (d, 1H, J=8.4 Hz), 4.97 (m, 1H), 4.86 (m, 2H), 4.80 (m, 1H), 4.10 (m, 2H), 3.07 (m, 2H), 2.25 (m, 2H), 1.94 (m, 1H), 1.70 (m, 2H), 1.57 (m, 1H), 1.44 (m, 2H), 1.32 (m, 2H). ESI(+)=552.4 (M+H)+; ESI(−)=550.3 (M−H)$^-$. Calculated mass: 551.21

(((S)-1-Carboxy-5-(3-(3-(1-(2-fluoroethyl)-1H-1,2,3-triazol-4-yl)phenyl)ureido)pentyl)carbamoyl)-L-glutamic acid (RPS-040)

RPS-040 was synthesized from alkyne (7) by the same method as RPS-042 and isolated as a white powder (82% yield). $^1$H NMR (500 MHz, DMSO-d6) δ 8.52 (s, 2H), 7.94 (s, 1H), 7.32 (m, 2H), 7.26 (m, 1H), 6.32 (m, 2H), 6.15 (t, 1H, J=5.2 Hz), 4.91 (t, 1H, J=4.6 Hz), 4.82 (t, 1H, J=4.6 Hz), 4.77 (t, 1H, J=4.6 Hz), 4.71 (t, 1H, J=4.6 Hz), 4.08 (m, 2H), 3.07 (d, 2H, $J_1$=12.4 Hz, $J_2$=6.8 Hz), 2.25 (m, 2H), 1.91 (m, 1H), 1.67 (m, 2H), 1.54 (m, 1H), 1.43 (m, 2H), 1.30 (m, 2H). ESI(+)=552.4 (M+H)+. ESI(−)=550.3. Calculated mass: 551.21

(((S)-1-Carboxy-5-(3-(4-(1-(2-fluoroethyl)-1H-1,2,3-triazol-4-yl)phenyl)ureido)pentyl)carbamoyl)-L-glutamic acid (RPS-041)

RPS-041 was synthesized from alkyne (8) by the same method as RPS-042 and isolated as a white powder (50% yield). $^1$H NMR (500 MHz, DMSO-d6) δ 8.57 (s, 1H), 8.48 (s, 1H), 7.70 (d, 2H, J=8.6 Hz), 7.47 (d, 2H, J=8.6 Hz), 6.35 (d, 1H, J=9.3 Hz), 6.33 (d, 1H, J=9.3 Hz), 6.22 (br s, 1H), 4.92 (t, 1H, J=4.7 Hz), 4.83 (t, 1H, J=4.7 Hz), 4.77 (t, 1H, J=4.7 Hz), 4.72 (t, 1H, J=Hz), 4.10 (m, 2H), 3.10 (m, 2H), 2.21 (m, 2H), 1.93 (m, 1H), 1.85 (m, 2H), 1.63 (m, 1H), 1.43 (m, 2H), 1.33 (m, 2H). ESI(+)=552.5 (M+H)+; ESI(−)=550.3 (M−H)$^-$. Calculated mass: 551.21

(((S)-1-Carboxy-5-(3-(2-((1-(2-fluoroethyl)-1H-1,2,3-triazol-4-yl)methoxy)phenyl)ureido)pentyl)carbamoyl)-L-glutamic acid (RPS-039)

RPS-039 was synthesized from alkyne (10) by the same method as RPS-042 and isolated as a white powder (34% yield). $^1$H NMR (500 MHz, DMSO-d6) δ 8.30 (s, 1H), 8.09 (d, 1H, J=9.7 Hz), 7.74 (s, 1H), 7.16 (d, 1H, J=9.6 Hz), 6.95 (t, 1H, J=5.4 Hz), 6.86 (m, 2H), 6.32 (m, 2H), 5.24 (s, 2H), 4.90 (t, 1H, J=4.4 Hz), 4.78 (m, 2H), 4.72 (t, 1H, J=4.4 Hz), 4.10 (m, 2H), 3.05 (m, 2H), 2.25 (m, 2H), 1.93 (m, 1H), 1.71 (m, 2H), 1.55 (m, 1H), 1.40 (m, 2H), 1.32 (m, 2H). ESI(+)=582.4 (M+H)$^+$; ESI(−)=580.3 (M−H)$^-$. Calculated mass: 581.22

(((S)-1-Carboxy-5-(3-(3-((1-(2-fluoroethyl)-1H-1,2,3-triazol-4-yl)methoxy)phenyl)ureido)pentyl)carbamoyl)-L-glutamic acid (RPS-043)

RPS-043 was synthesized from alkyne (11) by the same method as RPS-042 and isolated as a white powder (60% yield). $^1$H NMR (500 MHz, DMSO-d6) δ 8.40 (s, 1H), 8.25 (s, 1H), 7.18 (br s, 1H), 7.10 (t, 1H, J=8.1 Hz), 6.89 (d, 1H, J=8.1 Hz), 6.57 (d, 1H, J=8.2 Hz), 6.31 (m, 2H), 6.13 (br s, 1H), 5.09 (s, 1H), 4.87 (t, 1H, J=4.6 Hz), 4.76 (m, 2H), 4.69 (t, 1H, J=4.6 Hz), 4.08 (m, 2H), 3.05 (m, 2H), 2.24 (m, 2H), 1.91 (m, 1H), 1.69 (m, 2H), 1.55 (m, 1H), 1.40 (m, 2H), 1.31 (m, 2H). ESI(+)=582.4 (M+H)+; ESI(−)=580.2 (M−H)$^-$. Calculated mass: 581.22

(((S)-1-Carboxy-5-(3-(4-((1-(2-fluoroethyl)-1H-1,2,3-triazol-4-yl)methoxy)phenyl)ureido)pentyl)carbamoyl)-L-glutamic acid (RPS-038)

RPS-038 was synthesized from alkyne (12) by the same method as RPS-042 and isolated as a white powder (77% yield). $^1$H NMR (500 MHz, DMSO-d6) δ 8.27 (s, 1H), 8.25 (s, 1H), 7.30 (d, 2H, J=9.0 Hz), 6.91 (d, 2H, J=9.0 Hz), 6.34 (m, 2H), 6.10 (t, 1H, J=5.3 Hz), 5.09 (s, 2H), 4.89 (t, 1H, J=4.5 Hz), 4.78 (m, 2H), 4.71 (t, 1H, J=4.5 Hz), 4.10 (m, 2H), 3.06 (m, 2H), 2.25 (m, 2H), 1.93 (m, 1H), 1.73 (m, 2H), 1.60 (m, 1H), 1.42 (m, 2H), 1.32 (m, 2H). ESI(+)=582.3 (M+H)+; ESI(−)=580.3 (M−H)$^-$. Calculated mass: 581.22

Synthesis of DCFPyL in International Appl. No. PCT/US2017/039710

The synthesis of the cold ligand DCFPyL and the precursor trimethylammonium salt prosthetic group (20) were undertaken according to procedures described in Olberg D E, Arukwe J M, Grace D, Hjelstuen O K, Solbakken M, Kindberg G M, Cuthbertson A. One Step Radiosynthesis of 6-[$^{18}$F]Fluoronicotinic Acid 2,3,5,6-Tetrafluorophenyl Ester ([$^{18}$F]F-Py-TFP): A New Prosthetic Group for Efficient Labeling of Biomolecules with Fluorine-18. J Med Chem. 2010; 53:1732-40 and Chen Y, Pallumbhatla M, Foss C A, Byun Y, Nimmagadda S, Senthamizhchelvan S, et al. 2-(3-{1-Carboxy-5-[(6-[$^{18}$F]Fluoro-Pyridine-3-Carbonyl)-

Amino]-Pentyl}-Ureido)-Pentanedioic Acid, [$^{18}$F]DCFPyL, a PSMA-Based PET Imaging Agent for Prostate Cancer. Clin Cancer Res. 2011; 17:7645-53, each of which is incorporated herein by reference.

N,N,N-Trimethyl-5-((2,3,5,6-tetrafluorophenoy)-carbonyl)pyridine-2-aminium trifluoromethanesulfonate (20)

The title compound was isolated in three steps from 6-chloronicotinic acid as white crystals (137 mg, 19% yield). $^1$H NMR (500 MHz, CDCl$_3$) S 9.42 (d, 1H, J=2.2 Hz), 8.94 (dd, 1H, $J_1$=8.7 Hz, $J_2$=2.2 Hz), 8.29 (d, 1H, J=8.7 Hz), 7.57 (m, 1H), 3.76 (s, 9H). ESI(+)=329.3 (M$^+$-OTf). Calculated mass: 329.09

6-Fluoronicotinic acid 2,3,5,6-tetrafluorophenyl ester (21)

The title compound was synthesized from trimethylammonium salt (20) as a white powder (2.5 mg, 14% yield). $^1$H NMR (500 MHz, CDCl$_3$) δ 9.11 (d, 1H, J=2.1 Hz), 8.59 (dt, 1H, $J_1$=8.2 Hz, $J_2$=2.4 Hz), 7.15 (dd, 1H, $J_1$=8.6 Hz, $J_2$=2.9 Hz), 7.10 (m, 1H).

2-(3-{1-Carboxy-5-[(6-fluoropyridine-3-carbonyl)-amino]-pentyl}-ureido)-pentanedioic acid (DCFPyL)

The title compound was synthesized from the activated ester (21) in two steps as a white powder (2.0 mg, 55% yield). H NMR (500 MHz, DMSO-d6) δ 8.67 (m, 2H), 8.38 (m, 1H), 7.30 (dd, 1H, $J_1$=8.6 Hz, $J_2$=2.6 Hz), 6.33 (m, 2H), 4.08 (m, 2H), 3.26 (m, 2H), 2.25 (m, 2H), 1.93 (m, 1H), 1.72 (m, 2H), 1.58 (m, 3H), 1.36 (m, 2H). ESI(+)=499.4 (M+H)+. Calculated mass: 498.21

Radiosynthesis of Compounds of Int'l Appl. No. PCT/US2017/039710

General Methods

All solvents and reagents were purchased from Sigma Aldrich and were of reagent grade quality unless otherwise indicated. All reactions were carried out in oven dried glassware. Fluorine-18 was obtained by irradiation of H$_2$$^{18}$O (Rotem Industries) via the $^{18}$O(p,n)$^{18}$F transformation using a TR19 cyclotron (Advanced Cyclotron Systems, Inc.). End-of-bombardment activity was typically 5.55-9.25 GBq (150-250 mCi). Analytical and semi-preparative HPLC were performed on a dual pump Varian HPLC (Agilent Technologies) fitted with a dual UV-Vis detector and a NaI(T1) detector (Bioscan). Solvent A was 0.01% TFA in H$_2$O and solvent B was 0.01% TFA in 90:10 v/v MeCN:H$_2$O. Semi-prep HPLC was performed on a Bondapak C18 7.8×300 mm 125 Å column (Waters) while analytical HPLC was performed on a Symmetry C18 4.6×50 mm 100 Å column (Waters). The UV absorption spectrum was monitored at 220 nm and 280 nm. Semi-prep HPLC was performed using an isocratic solvent mixture of 15% B at a flow rate of 4 mL/min. Analytical HPLC was generally performed at a flow rate of 2 ml/min using the following gradient; 0% B 0-1 min., 0-100% B 1-8 mins., 100-0% B 8-10 mins. All radiochemical yields were corrected to the [$^{18}$F]fluoride activity measured at start-of-synthesis. The reaction conditions reported represent the highest yields obtained using manual radiosyntheses.

Radiosynthesis of Exemplary $^{18}$F Compounds of Int'l Appl. No. PCT/US2017/039710

A representative synthetic scheme for certain exemplary $^{18}$F compounds of Int'l Appl. No. PCT/US2017/039710 is presented below in Scheme 4. Particular procedural details follow thereafter.

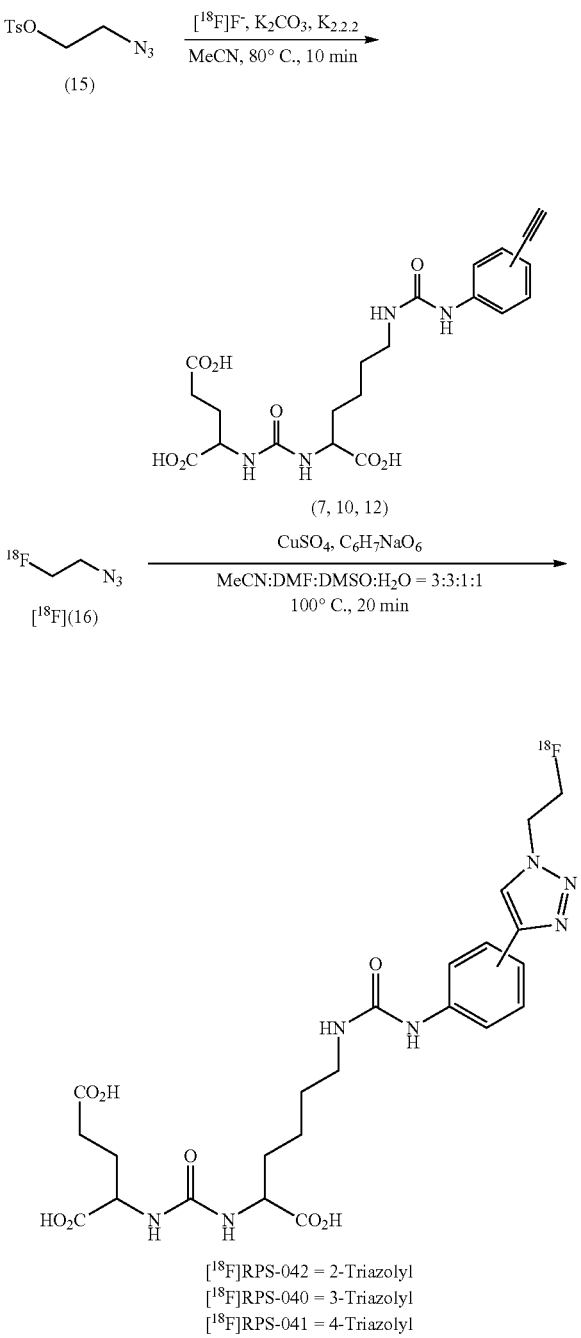

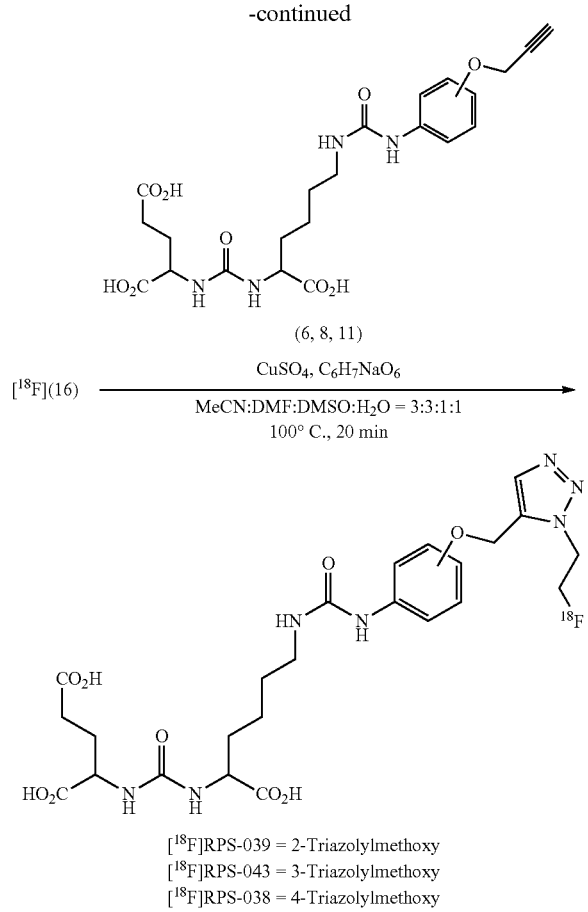

2-[$^{18}$F]fluoroethylazide (16)

No-carrier-added [$^{18}$F]fluoride was trapped on a pre-activated Sep-Pak QMA cartridge (Waters) and eluted with 1 mL of an 80% v/v MeCN/H$_2$O solution containing 2.7 mg K$_2$CO$_3$ and 4 mg Kryptofix-222. The solution was dried azeotropically with MCN (2×0.5 mL) at 100° C. in 10 min. To the dried [$^{18}$F]fluoride was added a solution of 2-azidoethyltosylate (15) (6 mg) in MCN (300 μL). The resulting solution was stirred at 80° C. for 10 min to yield 2-[$^{18}$F] fluoroethylazide. The 2-[$^{18}$F]fluoroethylazide was purified by distillation by heating the vial at 130° C. and trapping the 2-[$^{18}$F]fluoroethylazide in a vial containing 100 μL DMF cooled to 0° C.

Exemplary Synthesis of Representative IF Compounds of Int'l Appl. No. PCT/US2017/039710

A pre-mixed solution of 0.5M CuSO$_4$ (50 μL) and 1.5M sodium ascorbate (50 μL) in DMF (100 μL) was added to the vial containing the 2-[$^{18}$F]fluoroethylazide solution followed by 1 mg alkyne precursor (6-8; 10-12) in DMSO (100-150 μL). The reaction was stirred at 100° C. for 20 min. It was then cooled to room temperature, diluted with 2 mL H$_2$O and filtered through a 0.45 μm nylon syringe filter (Cole-Parmer). The filter was washed with 1 mL H$_2$O, which was added to the filtrate. The filtrate was purified by semi-prep reverse phase HPLC (4 mL/min; 0-100% B; 30 min), and the peak corresponding to $^{18}$F-labeled triazole was collected, diluted with H$_2$O and passed through a pre-activated Oasis™ solid phase extraction cartridge (Waters). The retained activity was eluted with EtOH and diluted with 0.9% NaCl solution until the concentration of ethanol was less than 5% v/v and the radioactivity concentration was a minimum of 74 MBq/mL. The synthesis, purification and final formulation were achieved in 105 min from start-of-synthesis. An optimized isocratic HPLC purification method (4 mL/min; 15% B; 30 min) was used to isolate [$^{18}$F]RPS-040 and [IF]RPS-041 in 20-40% decay corrected radiochemical yield, greater than 99% radiochemical purity and a specific activity of up to 391 GBq/μmol.

[$^{68}$Ga]Ga-PSMA-HBED-CC

The title compound was generated according to the procedure described in Amor-Coarasa A, Schoendorf M, Meckel M, Vallabhajosula S, Babich J. Comprehensive Quality Control of the ITG Ge-68/Ga-68 Generator and Synthesis of Ga-68-DOTATOC and Ga-68-PSMA-HBED-CC for Clinical Imaging. J Nucl Med. 2016 Apr. 21 (PMID: 27103024), incorporated herein by reference. In particular, a 1.85 GBq $^{68}$Ga/$^{68}$Ge Generator (ITG) was eluted with 4 mL 0.05M HCl, and $^{68}$GaCl$_3$ was obtained as a 185-222 MBq/mL solution. From this stock solution was taken 1 mL (containing approximately 185 MBq), which was combined with 5 μL of a 1 mg/mL solution of PSMA-HBED-CC (ABX) in H$_2$O at 95° C. The reaction was initiated by the addition of 20 μL of a 3N NaOAc solution, and heating to 95° C. continued for 20 min on a Thermomixer. It was then passed through a pre-activated Sep-Pak Oasis™ cartridge (Waters), and the cartridge was washed with H$_2$O. [$^{68}$Ga]Ga-PSMA-HBED-CC was eluted in a solution of 10% v/v EtOH in saline and diluted to a final concentration of approximately 100 MBq/mL. Decay-corrected radiochemical yield was greater than 95% and radiochemical purity was greater than 99%.

2-Azidoethanol (14)

Bromoethanol (250 mg, 2.0 mmol) was dissolved in H$_2$O (7 mL). A solution of sodium azide (195 mg, 3.0 mmol) in H$_2$O (3 mL) was added, and the reaction was stirred for 4 h at room temperature and then 16 h at 80° C. Then the reaction was cooled to room temperature and extracted with EtOAc. The organic layers were combined, dried over MgSO$_4$, filtered and concentrated under reduced pressure to give 2-azidoethanol (14) as a clear liquid (149 mg, 86% yield). $^1$H NMR (500 MHz, CDCl$_3$) δ 3.88 (t, 2H, J=5.1 Hz), 3.39 (t, 2H, J=5.1 Hz), 3.14 (br s, 1H).

2-Azidoethyltosylate (15)

A solution of p-toluenesulfonyl chloride (394 mg, 2.07 mmol) in CH$_2$Cl$_2$ (5 mL) was added to a solution of 2-azidoethanol (149 mg, 1.72 mmol) in CH$_2$Cl$_2$ (10 mL). Triethylamine (0.48 mL, 3.44 mmol) was added, and the reaction was stirred for 5 h at room temperature under Ar. Then the reaction was washed successively with 1M HCl, H$_2$O and saturated NaCl solution. The organic layer was dried over MgSO$_4$, filtered and concentrated under reduced pressure to give a pale oil. The oil was purified by silica chromatography (33% EtOAc in hexanes) to give 2-azidoethyltosylate (15) as a colorless oil (204 mg, 49% yield). $^1$H NMR (500 MHz, CDCl$_3$) δ 7.74 (d, 2H, J=8.2 Hz), 7.29 (d, 2H, J=8.1 Hz), 4.08 (t, 2H, J=5.1 Hz), 3.41 (t, 2H, J=5.1 Hz), 2.39 (s, 3H).

[$^{18}$F]DCFPyL 10.73 GBq (290 mCi) [$^{18}$F]Fluoride in 2 mL H$_2$$^{18}$O was dried azeotropically with MeCN at 100° C. in the presence of 50 µL of a 100 µg/mL solution of KF in H$_2$O and 4 mg kryptofix-222. To the dried mixture was added 9 mg 6-trimethylammonium salt (20) in 1 mL MeCN, and the reaction was stirred at 40° C. for 70 min. The reaction mixture was diluted with 10 mL and passed through a pre-activated Sep-Pak Silica cartridge (Waters). The eluate was evaporated to dryness at 60° C. To the dried mixture was added 1 mg di-tert-butyl (((S)-6-amino-1-(tert-butyoxy)-1-oxohexan-2-yl)carbamoyl)-L-glutamate (1) in 10 µL MeCN, 5 µL NEt$_3$ and 1 mL CH$_2$Cl$_2$. The reaction was stirred for 20 min at 40° C. and then another 1 mg (1) in 10 µL MCN and 5 µL NEt$_3$ were added. The reaction was stirred for a further 30 min before the solvent was evaporated and the crude product was dissolved in 100 µL TFA and stirred for 20 min at 40° C. The volatiles were evaporated under vacuum and the crude residue was dissolved in H$_2$O and purified by semi-prep HPLC (2 mL/min, 10 min gradient). The peak containing the product was collected, diluted with H$_2$O and trapped on a pre-activated Sep-Pak Oasis™ cartridge (Waters). The activity was eluted with 600 µL MeCN and concentrated at 100° C. under vacuum. The crude residue was dissolved in 200 µL 0.9% NaCl solution. Total synthesis time was 230 minutes, and decay corrected radiochemical yield was 0.9%, radiochemical purity was greater than 96% and the specific activity was greater than 35 GBq/µmol.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A $^{18}$F-labeled peptide ligand of any embodiment described herein, such as $^{18}$F-labeled somatostatin receptor agonist of any embodiment described herein, $^{18}$F-labeled bombesin receptor agonist of any embodiment described herein, $^{18}$F-labeled seprase binding compound of any embodiment described herein, and a compound of any embodiment of any one or more of Formulas I, IA, IB, II, IIA, III, IIIA, IV, IVA, V, VA, VI, and VIA as described herein.

B. An intermediate for preparing a $^{18}$F-labeled peptide ligand of Paragraph A, wherein the intermediate is of any embodiment described herein for preparing any one of $^{18}$F-labeled peptide ligands of the present technology.

C. A composition comprising a $^{18}$F-labeled peptide ligand of Paragraphs A and a pharmaceutically acceptable carrier.

D. A pharmaceutical composition for detecting a mammalian tissue expressing (e.g., overexpressing) a somatostatin receptor, a bombesin receptor, seprase, or a combination of any two or more thereof, the composition comprising an effective amount of the $^{18}$F-labeled peptide ligand of Paragraph A and a pharmaceutically acceptable carrier.

E. The pharmaceutical composition of Paragraph D, wherein the mammalian tissue comprises one or more of one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer.

F. A method comprising
administering a $^{18}$F-labeled peptide ligand of Paragraph A to a subject; and
subsequent to the administering, detecting one or more of positron emission, gamma rays from positron emission and annihilation, and Cerenkov radiation due to positron emission.

G. The method of Paragraph F, wherein the method comprises administering an effective amount of the $^{18}$F-labeled peptide ligand to the subject.

H. The method of Paragraph F or Paragraph G, wherein the subject is suspected of suffering from a mammalian tissue expressing (e.g., overexpressing) a somatostatin receptor, a bombesin receptor, seprase, or a combination of any two or more thereof, when administered to a subject.

I. The method of Paragraph J, wherein the mammalian tissue comprises one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer.

J. The method of any one of Paragraphs F-I, wherein administering the compound comprises parenteral administration.

K. A method of forming a $^{18}$F-labeled peptide ligand of Paragraph A, wherein the method comprises contacting in the presence of a solvent an intermediate of Paragraph B, a copper salt, and an azide of Formula XX

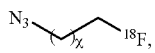
(XX)

where $\chi$ is independently at each occurrence 1 or 2.

What is claimed is:

1. A compound that is a $^{18}$F-labeled somatostatin receptor agonist according to Formula I

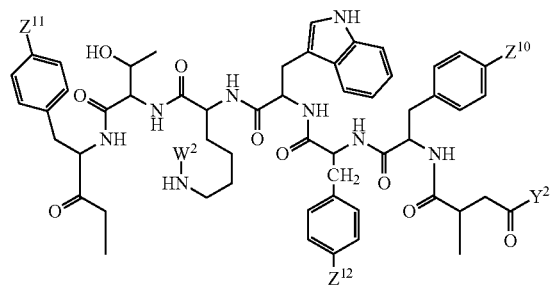
(I)

-continued

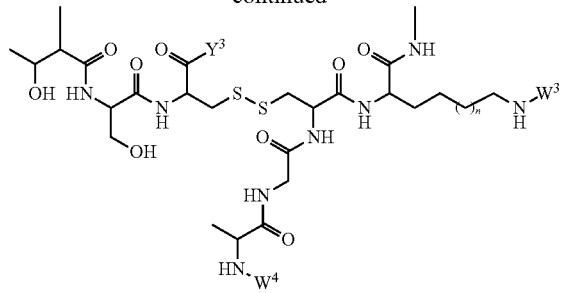

or a pharmaceutically acceptable salt and/or solvate thereof, wherein $Z^{10}$, $Z^{11}$, and $Z^{12}$ are each independently OH;

$W^4$ is H;

one of $W^2$ and $W^3$ is

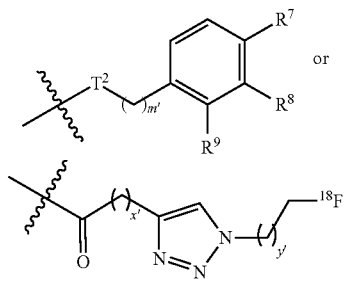

or one of $Y^2$ and $Y^3$ is

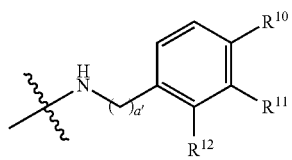

and the remaining $W^2$ and $W^3$ is H and the remaining $Y^2$ and $Y^3$ is OH or $NH_2$;

wherein $T^2$ is —C(O)— or —C(O)NH—, one of $R^7$, $R^8$, and $R^9$ and one of $R^{10}$, $R^{11}$, and $R^{12}$ is

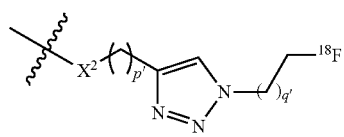

and the remaining two of $R^7$, $R^8$, and $R^9$ are each H and the remaining two of $R^{10}$, $R^{11}$, and $R^{12}$ are each H;

$X^2$ is absent, O, S, or NH;

m' and a' are each independently 0, 1, 2, or 3;

n is 0 or 1;

p' is 0, 1, 2, or 3, provided that when p' is 0 then $X^2$ is absent;

q' is 1 or 2; x' is 0, 1, 2, or 3; and y' is 1 or 2.

2. The compound of claim 1, wherein the compound is of Formula IA

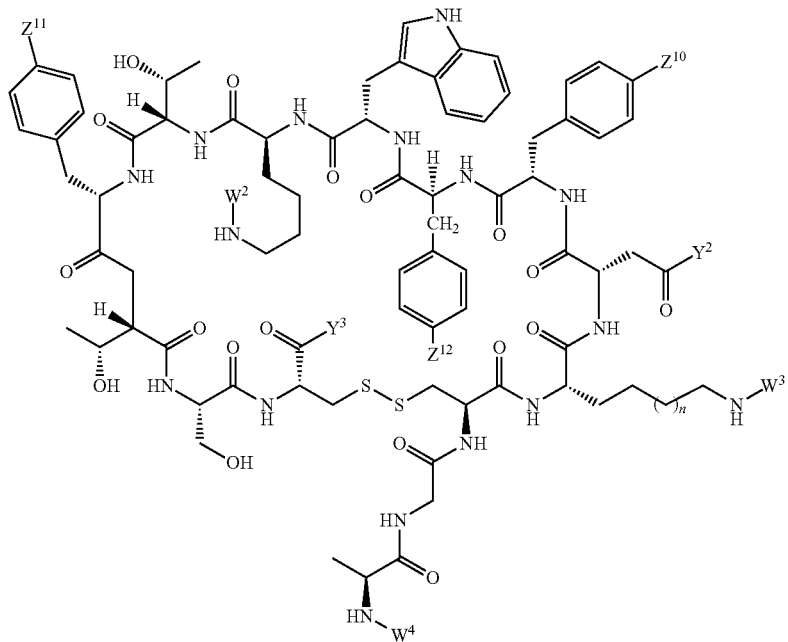
(IA)
or a pharmaceutically acceptable salt and/or solvate thereof.
3. A method comprising
administering a compound of claim 1 to a subject; and
subsequent to the administering, detecting one or more of positron emission, gamma rays from positron emission and annihilation, and Cerenkov radiation due to positron emission.
* * * * *